(12) United States Patent
Yulai et al.

(10) Patent No.: US 9,056,058 B2
(45) Date of Patent: Jun. 16, 2015

(54) MICROCAPSULES WITH IMPROVED SHELLS

(75) Inventors: Jin Yulai, Battle Creek, MI (US); Colin James Barrow, Halifax (CA); Wei Zhang, Halifax (CA); Cuie Yan, Dartmouth (CA); Jonathan Michael Curtis, Alberta (CA); Shawn Moulton, Lakeside (CA); Nancy Beatrice Djogbenou, Halifax (CA); Lesek Alexa Demont, Chester (CA)

(73) Assignee: DSM Nutritional Products, Kaiseraugst (CH)

( * ) Notice: Subject to any disclaimer, the term of this patent is extended or adjusted under 35 U.S.C. 154(b) by 930 days.

(21) Appl. No.: 12/308,045

(22) PCT Filed: Jun. 4, 2007

(86) PCT No.: PCT/IB2007/003358
§ 371 (c)(1),
(2), (4) Date: Sep. 24, 2009

(87) PCT Pub. No.: WO2008/017962
PCT Pub. Date: Feb. 14, 2008

(65) Prior Publication Data
US 2010/0173002 A1    Jul. 8, 2010

Related U.S. Application Data

(60) Provisional application No. 60/837,050, filed on Aug. 11, 2006, provisional application No. 60/879,759, filed on Jan. 10, 2007, provisional application No. 60/811,024, filed on Jun. 5, 2006.

(51) Int. Cl.
| | |
|---|---|
| A61K 31/575 | (2006.01) |
| A61P 35/00 | (2006.01) |
| A61P 37/08 | (2006.01) |
| A61P 9/02 | (2006.01) |
| A61K 9/16 | (2006.01) |
| A61K 9/10 | (2006.01) |
| A61K 31/202 | (2006.01) |
| A61P 9/00 | (2006.01) |
| A61K 31/232 | (2006.01) |
| A61K 9/50 | (2006.01) |
| A23L 1/00 | (2006.01) |
| A23L 1/30 | (2006.01) |
| A23L 1/304 | (2006.01) |
| A23L 1/305 | (2006.01) |

(52) U.S. Cl.
CPC ............ *A61K 9/5057* (2013.01); *A23L 1/0029* (2013.01); *A23L 1/30* (2013.01); *A23L 1/3002* (2013.01); *A23L 1/3006* (2013.01); *A23L 1/304* (2013.01); *A23L 1/3056* (2013.01); *A23V 2002/00* (2013.01); *A61K 9/1658* (2013.01)

(58) Field of Classification Search
None
See application file for complete search history.

(56) References Cited

U.S. PATENT DOCUMENTS

| | | | |
|---|---|---|---|
| 2,800,457 A | 7/1957 | Green et al. | 428/402.2 |
| 2,800,458 A | 7/1957 | Green | |
| 3,041,289 A | 6/1962 | Katchen et al. | |
| 3,179,600 A | 4/1965 | Brockett | 503/200 |
| 3,190,837 A | 6/1965 | Brynko | |
| 3,526,682 A | 9/1970 | Timreck | 264/4 |
| 3,697,437 A | 10/1972 | Fogel et al. | 427/213.33 |
| 4,010,038 A | 3/1977 | Iwasaki et al. | 430/550 |
| 4,217,370 A | 8/1980 | Rawlings et al. | 426/98 |
| 4,219,439 A | 8/1980 | Miyake et al. | 264/4.4 |
| 4,222,891 A | 9/1980 | Okimoto et al. | 264/4.4 |
| 4,232,084 A | 11/1980 | Tate | |
| 4,273,672 A | 6/1981 | Vassiliades | 264/4.1 |
| 4,442,051 A * | 4/1984 | Rowe et al. | 264/4.3 |
| 4,485,172 A | 11/1984 | Gierhart | 435/134 |
| 4,670,247 A | 6/1987 | Scialpi | 424/16 |
| 4,695,466 A | 9/1987 | Morishita et al. | 424/456 |
| 4,744,933 A | 5/1988 | Rha et al. | 264/4.3 |
| 4,749,620 A | 6/1988 | Rha et al. | 428/402.2 |
| 4,808,408 A | 2/1989 | Baker et al. | 424/408 |
| 4,851,339 A | 7/1989 | Hills | 435/67 |
| 4,861,627 A | 8/1989 | Mathiowitz et al. | 427/213.31 |
| 4,867,986 A | 9/1989 | Desai et al. | 424/464 |
| 4,891,172 A | 1/1990 | Matsushita et al. | 264/4.33 |
| 4,895,725 A | 1/1990 | Kantor et al. | 424/455 |
| 4,923,855 A | 5/1990 | Jensen | 514/188 |
| 4,946,624 A | 8/1990 | Michael | 510/101 |
| 4,954,492 A | 9/1990 | Jensen | 514/188 |
| 4,963,367 A | 10/1990 | Ecanow | 424/485 |

(Continued)

FOREIGN PATENT DOCUMENTS

| | | |
|---|---|---|
| CA | 2318539 A1 | 7/1999 |
| CA | 2447002 | 4/2003 |

(Continued)

OTHER PUBLICATIONS

Vandenberg et al. "Factors affecting protein release from alginate-chitosan coacervate microcapsules during producting and gastric/intestinal simulation" Journal of Controlled Release, 77, 2001, pp. 297-307.*

(Continued)

*Primary Examiner* — Kortney L Klinkel
*Assistant Examiner* — Melissa Javier
(74) *Attorney, Agent, or Firm* — Meunier Carlin & Curfman LLC

(57) ABSTRACT

Disclosed are microcapsules and methods for preparing and using them, as well as methods for improving various properties of microcapsules like impermeability.

17 Claims, 9 Drawing Sheets

(56) References Cited

U.S. PATENT DOCUMENTS

| | | |
|---|---|---|
| 5,035,896 A | 7/1991 | Aptel et al. ............. 424/456 |
| 5,051,304 A | 9/1991 | David et al. ............. 428/402.2 |
| 5,059,622 A | 10/1991 | Sears ............................. 514/549 |
| 5,130,061 A | 7/1992 | Cornieri ...................... 260/420 |
| 5,156,956 A | 10/1992 | Motoki ...................... 435/68.1 |
| 5,194,615 A | 3/1993 | Jensen ............................ 546/5 |
| 5,204,029 A | 4/1993 | Morgan et al. ............... 264/4.4 |
| 5,330,778 A | 7/1994 | Stark ............................ 426/531 |
| 5,356,636 A | 10/1994 | Schneider .................... 424/489 |
| 5,378,413 A | 1/1995 | Mihm et al. .................. 264/4.3 |
| 5,428,014 A | 6/1995 | Labroo ........................... 514/12 |
| 5,456,985 A | 10/1995 | Zgoulli et al. ............. 428/402.2 |
| 5,573,934 A | 11/1996 | Hubbell et al. ............... 435/177 |
| 5,603,952 A | 2/1997 | Soper ............................ 424/456 |
| 5,603,961 A | 2/1997 | Suzuki et al. ................ 424/502 |
| 5,670,209 A | 9/1997 | Wyckoff ...................... 427/215 |
| 5,700,397 A | 12/1997 | Maeda et al. .............. 428/402.24 |
| 5,759,599 A | 6/1998 | Wampler et al. ............... 426/89 |
| 5,766,637 A | 6/1998 | Shine et al. ................... 424/497 |
| 5,780,056 A * | 7/1998 | Akamatsu et al. ............ 424/464 |
| 5,788,991 A | 8/1998 | Nastke et al. |
| 5,827,531 A | 10/1998 | Morrison et al. ............. 424/450 |
| 5,855,826 A | 1/1999 | Lee et al. |
| 5,872,140 A | 2/1999 | Hesse et al. ................... 514/359 |
| 5,993,851 A | 11/1999 | Foldvari ....................... 424/450 |
| 5,997,863 A | 12/1999 | Zimmermann ............. 424/94.5 |
| 6,019,988 A | 2/2000 | Nomoto et al. .............. 424/400 |
| 6,020,200 A | 2/2000 | Enevold ....................... 435/382 |
| 6,039,901 A | 3/2000 | Soper ............................. 264/4.3 |
| 6,063,820 A | 5/2000 | Cavazza ........................ 514/739 |
| 6,103,378 A | 8/2000 | Yao et al. ................... 428/402.2 |
| 6,106,875 A | 8/2000 | Soper et al. |
| 6,221,401 B1 | 4/2001 | Zasadzinski et al. ......... 424/490 |
| 6,234,464 B1 | 5/2001 | Krumbholz et al. ......... 264/4.32 |
| 6,235,951 B1 | 5/2001 | Sakyu et al. .................. 570/156 |
| 6,274,174 B1 | 8/2001 | Hom-ma et al. ............. 424/489 |
| 6,300,377 B1 | 10/2001 | Chopra ........................ 514/715 |
| 6,325,951 B1 | 12/2001 | Soper et al. ................... 264/4.3 |
| 6,328,995 B1 | 12/2001 | Bewert et al. ................ 424/489 |
| 6,365,176 B1 | 4/2002 | Bell et al. ..................... 424/439 |
| 6,417,233 B1 | 7/2002 | Sears et al. ................... 514/549 |
| 6,441,050 B1 | 8/2002 | Chopra ........................ 514/675 |
| 6,482,433 B1 | 11/2002 | DeRoos et al. ............... 424/464 |
| 6,528,165 B2 | 3/2003 | Chandler ................... 428/402.2 |
| 6,534,091 B1 | 3/2003 | Garces et al. ................ 424/489 |
| 6,534,094 B2 | 3/2003 | Moyano et al. .............. 424/491 |
| 6,544,926 B1 | 4/2003 | Bodmer et al. ............... 503/215 |
| 6,630,157 B1 | 10/2003 | Horrobin et al. ............. 424/439 |
| 6,652,891 B2 | 11/2003 | Selzer ........................... 424/757 |
| 6,861,458 B2 | 3/2005 | Smith et al. .................. 523/160 |
| 6,867,471 B2 | 3/2005 | Goller et al. ................. 257/501 |
| 6,969,530 B1 * | 11/2005 | Curtis et al. ................. 424/489 |
| 6,972,592 B2 | 12/2005 | Benware ........................ 326/38 |
| 6,974,592 B2 | 12/2005 | Yan ............................. 424/489 |
| 7,727,692 B2 | 6/2010 | Yan |
| 2003/0044380 A1 | 3/2003 | Zhu et al. ..................... 424/443 |
| 2003/0078617 A1 | 4/2003 | Schwartz et al. |
| 2003/0091654 A1 | 5/2003 | Katz et al. .................... 424/486 |
| 2003/0193102 A1 * | 10/2003 | Yan ............................... 264/4.1 |
| 2004/0106591 A1 | 6/2004 | Pacioretti et al. ................ 435/6 |
| 2005/0019416 A1 | 1/2005 | Yan ............................. 424/489 |
| 2005/0067726 A1 | 3/2005 | Yan et al. ................... 428/402.2 |
| 2005/0118285 A1 | 6/2005 | Lacoutiere |
| 2005/0249952 A1 | 11/2005 | Vasishtha et al. |
| 2007/0027028 A1 | 2/2007 | Pears et al. .................. 568/902.2 |
| 2007/0059340 A1 | 3/2007 | Belloe et al. ................. 424/439 |
| 2007/0078071 A1 | 4/2007 | Lee .............................. 510/441 |
| 2007/0141211 A1 | 6/2007 | Kolar et al. .................. 427/201 |
| 2007/0224216 A1 | 9/2007 | Teas |
| 2009/0274791 A1 | 11/2009 | Mattson |
| 2010/0055281 A1 | 3/2010 | Barrow |
| 2010/0173002 A1 | 7/2010 | Jin |

FOREIGN PATENT DOCUMENTS

| | | |
|---|---|---|
| DE | 1035319 | 7/1958 |
| EP | 0 301 777 A1 | 2/1989 |
| EP | 0 416 575 A2 | 3/1991 |
| EP | 0426428 | 5/1991 |
| EP | 0 434 760 B1 | 7/1991 |
| EP | 0 644 771 B2 | 3/1995 |
| EP | 0 745 670 A1 | 12/1996 |
| EP | 0 782 883 A2 | 7/1997 |
| EP | 0 821 881 A2 | 2/1998 |
| EP | 0 856 355 A2 | 8/1998 |
| EP | 1 116 516 A1 | 7/2001 |
| EP | 0 821 881 B1 | 9/2001 |
| EP | 1237423 | 9/2002 |
| EP | 0 982 038 B1 | 1/2003 |
| EP | 1430947 A1 | 6/2004 |
| EP | 1357977 | 7/2004 |
| EP | 0 897 970 B1 | 9/2004 |
| GB | 1198412 | 7/1970 |
| GB | 2 091 286 | 7/1982 |
| GB | 2 115 768 | 9/1983 |
| JP | 5394273 A | 8/1978 |
| JP | 58028234 | 2/1983 |
| JP | 58149645 | 6/1983 |
| JP | 61172807 | 8/1986 |
| JP | 1148338 | 6/1989 |
| JP | 2086743 | 3/1990 |
| JP | 02-257845 | 10/1990 |
| JP | 02-261534 | 10/1990 |
| JP | 5292899 | 11/1993 |
| JP | 09-302379 | 11/1997 |
| JP | 2002/028473 | 1/2002 |
| JP | 2005/522313 | 7/2005 |
| JP | 2006/506410 | 2/2006 |
| WO | WO 91/06287 | 5/1991 |
| WO | WO 92/11083 | 7/1992 |
| WO | WO 97/13416 | 4/1997 |
| WO | WO 97/40701 | 11/1997 |
| WO | WO 01/80656 | 11/2001 |
| WO | WO 02/096408 | 12/2002 |
| WO | WO03086104 A1 | 10/2003 |
| WO | WO 03/105606 | 12/2003 |
| WO | WO 03/106014 | 12/2003 |
| WO | WO 2004/041251 | 5/2004 |
| WO | 2004/054702 | 7/2004 |
| WO | WO2007054207 A1 | 5/2007 |
| WO | WO2007055815 A1 | 5/2007 |

OTHER PUBLICATIONS

Jizomoto, "Phase Separation Induced In Gelatin-Base Coacervation System by Addition of Water-soluble nonionic Polymers I: Microencapsulation", Journal of Pharmaceutical Sciences, 73(7), 1984, pp. 879-882.*

Calon F, Lim GP, Yang F, Morihara T, Teter B, Ubeda O, Rostaing P, Triller A, Salem N Jr, Ashe KH, Frautschy SA, Cole GM. (2004) Docosahexaenoic acid protects from dendritic pathology in an Alzheimer's disease mouse model. Neuron. 43(5): 633-45.

Choi SS, Regenstein JM. (2000) Physicochemical and sensory characteristics of fish gelatin. J Food Sci: 65(2): 194-199.

Dyerberg J, Madsen P, Moller J, Aardestrup I, Schmidt EB. (1995) Bioavailability of n-3 Fatty Acid Formulations, in *Omega-3 fatty acids: prevention and treatment of vascular disease*, Kristensen et al., Eds., Bi & Gi Publ., Verona-Springer-Verlag, London, pp. 217-226.

Fong JW. (1988). Microencapsulation by solvent and organic phase separation processes, in *Controlled Release Systems: Fabrication Technology*, Hsieh DS, Ed., CRC Press, New York, pp. 99-105.

Gruppo Italiano per lo Studio della Sopravvivenza nell'Infarto miocardico. (1999) Dietary supplementation with n-3 polyunsaturated fatty acids and vitamin E after myocardial infarction: results of the GISSI-Prevenzione trial. Lancet. 354(9177): 447-55. Erratum in: (2001) 357(9256): 642 and (2007) 369(9556): 106.

Goyer RA (1991). Toxic effects of metals, in, *Casarett and Doull's Toxicology*, Amdur et al., Eds., 4$^{th}$ ed., Pergamon Press, New York, pp. 638-680.

(56) References Cited

OTHER PUBLICATIONS

Harris WS. (2005) Extending the cardiovascular benefits of omega-3 Fatty acids. Curr Atheroscler Rep. 7(5): 375-80.
Haug I, Draget KI, Smidsrod O. (2004) Physical and rheological properties of fish gelatin compared to mammalian gelatin. Food Hydrocolloids, 18:203-213.
Holub BJ. (2002) Clinical nutrition: 4. Omega-3 fatty acids in cardiovascular care. CMAJ. 166(5): 608-15.
http://en.wikipedia.org/wiki/morula.
http://www.advancedfertility.com/4cell.htm.
http://www.advancedfertility.com/8cell.htm.
http://www.advancedfertility.com/morula.htm.
Bohnet et al., Ullmann's Encyclopedia of Industrial Chemistry, vol. II, p. 668, right col. (2003).
Examination report for Application No. 200780019734.2 dated May 6, 2011.
Examination report for Application No. MX/a/2008/012967 dated Apr. 27, 2011.
Examination report for Application No. 200780029069.5 dated Feb. 24, 2011.
Examination report for Application No. 07825594.0 dated Mar. 30, 2011.
Examination report for Application No. 200880007740.0 dated Mar. 23, 2011.
Examination report for Application No. 2003-583137 dated May 10, 2011.
LIMMER, "Remington:The Science and Practice of Pharmacy," p. 332, left col. (2000).
Notice of Allowance for U.S. Appl. No. 11/227,961 dated Jun. 14, 2011.
Reasons for Submission on behalf of Japan Capsular Products Inc. filed in Japanese Patent Application No. 2003-583137 on Nov. 26, 2010.
Response to Opposition for Application No. EP06020381.7 dated Jun. 29, 2011.
Examination Report for Japanese Application No. 2008-520263 dated Feb. 22, 2011.
Examination Report for European Application No. 07 754 635.6 dated Aug. 26, 2011.
Examination Report for Application No. 565606 dated May 13, 2010.
Examination Report for Application No. 573327 dated Nov. 16, 2011.
Examination Report for Application No. 596403 dated Nov. 16, 2011.
Office Action for Application No. 200780029069.5 dated Feb. 24, 2011.
Office Action for Application No. 08713076.1 dated Sep. 21, 2011.
Office Action for Application No. 7007996/2005 dated Nov. 4, 2011.
Office Action for U.S. Appl. No. 11/918,150 dated Nov. 16, 2011.
Office Action for U.S. Appl. No. 11/988,320 dated Sep. 1, 2011.
Office Action for Application No. AU 2007282922 dated Mar. 2, 2012.
Office Action for Application No. AU 2007238985 dated Dec. 5, 2011.
Office Action for Application No. CN 200780029069.5 dated Apr. 27, 2012.
Office Action for Application No. CN 200780019734.2 dated Apr. 25, 2012.
Office Action for Application No. CN 200880007740.0 dated Mar. 16, 2012.
Office Action for Application No. EP 07825594.0 dated Aug. 31, 2011.
Office Action for Application No. EP 07754635.6 dated Dec. 21, 2009.
Office Action for Application No. EP 07754635.6 dated Mar. 6, 2012.
Office Action for Application No. EP 11196119.9 dated Mar. 1, 2012.
Office Action for Application No. JP 2003-583137 dated Jan. 24, 2012.
Office Action for Application No. JP 2009-504244 dated Feb. 20, 2011.
Office Action for Application No. KR 10-2011-7022451 dated Dec. 22, 2011.
Office Action for Application No. MX/a/2008/015556 dated Mar. 15, 2012.
Office Action for Application No. NZ 573327 dated Dec. 8, 2011.
Office Action for Application No. NZ 578872 dated Nov. 11, 2011.
Office Action for Application No. NZ 572529 dated May 21, 2010.
Response to Office Action for NZ 572529 dated Oct. 1, 2010.
Office Action for Application No. NZ 572529 dated Oct. 22, 2010.
Office Action for Application No. PE 000110-2008 dated Feb. 29, 2012.
Office Action for U.S. Appl. No. 12/226,041 dated Mar. 29, 2012.
Office Action for U.S. Appl. No. 11/988,320 dated Jan. 19, 2012.
Office Action for U.S. Appl. No. 11/435,605 dated Sep. 2, 2010.
Response to Office Action for U.S. Appl. No. 11/435,605 dated Nov. 5, 2010.
Office Action for U.S. Appl. No. 11/435,605 dated Jan. 24, 2011.
Response to Office Action for U.S. Appl. No. 11/435,605 dated Apr. 13, 2011.
Schrooyen et al., Microencapsulation: its application in nutrition, Proceedings of the Nutrition Society, 60:475-479 (2001).
Office Action for Application No. EP 07 825 594.0 dated Feb. 14, 2013.
Chourpa, Igor, et al., "Conformational Modifications of α Gliadin and Globulin Proteins upon Complex Coacervates Formation with Gum Arabic as Studied by Raman Microspectroscopy," Biomacromolecules, vol. 7, 2006, pp. 2616-2623.
Office Action for U.S. Appl. No. 13/009,418 dated Jun. 21, 2013.
Office Action for U.S. Appl. No. 12/522,826 dated Jul. 2, 2013.
Office Action for U.S. Appl. No. 12/768,152 dated Jul. 25, 2013.
Office Action for Application No. CN 200780029069.5 dated Sep. 24, 2013.
Office Action for Application No. JP 2009523371 dated Oct. 17, 2013.
Office Action for Application No. KR 1020097000087 dated Oct. 18, 2013 (English Translation).
Office Action for Application No. EP 08713076.1 dated Feb. 18, 2013.
Boh et al., "Microcapsule Applications: Patent and Literature Analysis," MML Series, 6:85-156 (2003).
BORGHI, "Omega-3 LC PUFAs, A new solution for pasterurized milk enrichment," Wellness Foods Europe, pp. 25-26 (May 2005).
Encyclopedia of Pharmaceutical Technology, "Micoencapsulation," Editors; James Swarbrick and James C. Boylan, Marcel Dekker, Inc., New York, vol. 9, pp. 423-441, 1994.
European Patent Office European Search Report for 06020381.7 dated Apr. 10, 2007.
GISSI-Prevenzione Investigators, "Dietary supplementation with Omega-3 polyunsaturated fatty acids and vitamin E after myocardial infarction: results of the GISSI-Prevenzione trial," Lancet, 354:447-455 (1999).
International Search Report and Written Opinion for PCT/US08/000301 mailed Apr. 30, 2008.
International Search Report and Written Opinion for PCT/US07/008138 mailed May 9, 2008.
International Search Report and Written Opinion for PCT/IB07/03358 mailed Apr. 25, 2008.
European Search Authority International Search Report for PCT/IB2006/001214 and Written Opinion mailed Feb. 8, 2007.
International Search Report and Written Opinion for PCT/IB06/01526 mailed Aug. 22, 2006.
Kondo et al., "Microencapsulation utilizing phase separation from an aqueous solution system," Microcapsule Processing and Technology, Marcel Dekker Inc., New York, pp. 70-95 (1979).
Leclercq et al., "Formation and characterization of microcapsules by complex coacervation with liquid or solid aroma cores," Flavour Fragr. J., 24:17-24 (2009).
Magdassi et al., "Microencapsulation of Oil-in-Water Emulsions by Proteins," Microencapsulation—Methods and Industrial Applications, edited by Simon Benita, Marcel Dekker, Inc., New York, pp. 21-33 (1996).
Opposition against EP1492417, 2008.
Response to Opposition against EP1492417, 2008.

(56) References Cited

OTHER PUBLICATIONS

Yoshida et al., "Manufacture of microcapsules from complex coacervation processes," Chemical Abstract, Accession No. 140735 (1990).
Appel LJ, Miller ER 3rd, Seidler AJ, Whelton PK. (1993) Does supplementation of diet with 'fish oil' reduce blood pressure? A meta-analysis of controlled clinical trials. Arch Intern Med. 153(12): 1429-38.
Barrow C, Nolan C, Jin Y. (2007) Stabilization of highly unsaturated fatty acids and delivery into foods. Lipid Tech. 19(5): 108-111.
Beestman G. (2000) Microencapsulation of solid particles, Abstracts of Papers, 220th ACS National Meeting, Washington, DC, United States, Aug. 20-24, 2000.
Hu M, McClements DJ, Decker EA. (2004) Impact of chelators on the oxidative stability of whey protein isolate-stabilized oil-in-water emulsions containing ω-3 fatty acids. Food Chem. 88(1): 57-62.
Ijichi K, Yoshizawa H, Uemura Y, Hatate Y, Kawano Y. (1997) Multi-layered gelatin/acacia microcapsules by complex coacervation method. J Chem Eng Jpn. 30(5): 793-98.
Kage H, Kawahara H, Ogura H, Matsuno Y. (1997) Microencapsulation of mono-dispersed droplets by complex coacervation and membrane thickness of generated capsules. Accession No. 1997:615273 CAPLUS.
Kas and Oner, "Microencapsulation using coacervation/phase separation," In Handbook of Pharmaceutical Controlled Release Technology, Wise Ed., Marcel Dekker Inc., New York, pp. 301-328, 2000.
Knoth A, Scherze I, Muschiolik G. (2005) Stability of water-in-oil-emulsions containing phosphatidylcholine-depleted lecithin. Food Hydrocolloids. 19(3): 635-40.
Kondo et al. "Microencapsulation utilizing phase separation from an aqueous solution system," In "Microcapsule Processing and Technology", Marcel Dekker Inc., New York, pp. 70-95, 1979.
Kris-Etherton PM, Harris WS, Appel LJ. (2002) Fish consumption, fish oil, omega-3 fatty acids, and cardiovascular disease. Circulation. 106(21): 2747-57. Erratum in: Circulation. (2003) 107(3): 512.
Marcus and Coulston, "The Vitamins," In: Gilman et al., eds., Goodman and Gilman's the pharmacological basis of therapeutics, McGraw-Hill, Inc., New York, pp. 1524-1529, 1990.
Mori TA, Burke V, Puddey IB, Watts GF, O'Neal DN, Best JD, Beilin LJ. (2000) Purified eicosapentaenoic and docosahexaenoic acids have differential effects on serum lipids and lipoproteins, LDL particle size, glucose, and insulin in mildly hyperlipidemic men. Am J Clin Nutr. 71(5): 1085-94.
Muskiet FA, Fokkema MR, Schaafsma A, Boersma ER, Crawford MA. (2004) Is docosahexaenoic acid (DHA) essential? Lessons from DHA status regulation, our ancient diet, epidemiology and randomized controlled trials. J Nutr. 134(1): 183-86.
O'Keefe JH, Harris WS. (2000) Omega-3 fatty acids: time for clinical implementation? Am J Cardiol. 85(10): 1239-41.
Onuki Y, Morishita M, Takayama K, Tokiwa S, Chiba Y, Isowa K, Nagai T. (2000) In vivo effects of highly purified docosahexaenoic acid on rectal insulin absorption. Int J Pharm. 198(2): 147-56.
Ovide-Bordeaux S, Grynberg A. (2004) Docosahexaenoic acid affects insulin deficiency- and insulin resistance-induced alterations in cardiac mitochondria. Am J Physiol Regul Integr Comp Physiol. 286(3): R519-27.
Radack K, Deck C, Huster G. (1991) The effects of low doses of n-3 fatty acid supplementation on blood pressure in hypertensive subjects. A randomized controlled trial. Arch Intern Med. 151(6): 1173-80.
Recommended Dietary Allowances, Ninth Revised Edition, *The National Academy of Sciences*, $9^{th}$ Revised Edition, p. 159-160, 1980.
Soper, "Utilization of coacervated flavors," in "Encapsulation and Controlled Release of Food Ingredients," Risch and Reineccius Ed., ACS Symposium Series 590, Washington DC, pp. 104-112, 1995.
Sparks, "Microencapsulation," In "Kirk-Othmer, Encyclopedia of Chemical Technology," vo. 15, $3^{rd}$ Ed., John Wiley & Sons Inc., New York, pp. 470-793, 1981.
Sugano M. (2001) Balanced intake of polyunsaturated fatty acids for health benefits. J Oleo Sci. 50(5): 305-11.
Thimma RT, Tammishetti S. (2003) Study of complex coacervation of gelatin with sodium carboxymethyl guar gum: microencapsulation of clove oil and sulphamethoxazole. J Microencapsul. 20(2): 203-10.
Webb D. Alternative sources of omega-3 fatty acids. *Natural Foods Merchandiser*, Aug. 1, 2005, available at http://www.naturalfoodsmerchandiser.com/tabId/106/itemId/1692/Alternative-sources-of-omega3-fatty-acids.aspx.
Whorton and Reineccius, "Evaluation of the mechanisms associated with the release of encapsulated flavor material form maltodextrin matrices," In "Encapsulation and Controlled Release of Food Ingredients," Risch and Reineccius Ed., ACS Symposium Series 590, Washington DC, 143-160, 1995.
Office Action for CA Application No. 2654031 dated Feb. 25, 2014.
Office Action for CN Application No. 200780029069.5 dated Apr. 21, 2014.
Office Action for JP Application No. P2009-523371 dated May 13, 2014.
Office Action for JP Application No. P2013-063698 dated Jun. 3, 2014.
Office Action for KR Application No. 2009-7000087 dated Jun. 5, 2014.
Examination Report for EP Application No. 07825594.0, date Sep. 4 2014.
JIZOMOTO, Phase Separation Induced in Gelatin-Based Coacervation Systems by Addition of Water-Soluble Nonionic Polymers II: Effect of Molecular Weight, J. Pharm. Sci.,1985, 74:469-472.
Office Action, dated Nov. 19, 2014, received in connection with CA Application No. 2654031.

\* cited by examiner a.

b.

c.

d.

NaAs = sodium ascorbate.

MICROCAPSULES WITH IMPROVED SHELLS

CROSS REFERENCE TO RELATED APPLICATIONS

This application claims the benefit of priority to U.S. Provisional Application No. 60/811,024, filed on Jun. 5, 2006, U.S. Provisional Application No. 60/837,050, filed on Aug. 11, 2006, and U.S. Provisional Application No. 60/879,759, filed on Jan. 10, 2007, all of which are incorporated by reference herein in their entireties.

BACKGROUND

Microcapsules are small particles of solids or droplets of liquids inside a thin coating of a shell material such as beeswax, starch, gelatin, or polyacrylic acid. They are used, for example, to prepare liquids as free-flowing powders or compressed solids, to separate reactive materials, to reduce toxicity, to protect against oxidation and/or to control the rate of release of a substance such as an enzyme, a flavor, a nutrient, a drug, etc.

In the past, research has concentrated on so-called "single-core" microcapsules. However, one of the problems with single-core microcapsules is their susceptibility to rupture. Thus, others have tried to increase the thickness of the microcapsule wall in order to increase the strength and/or impermeability of such microcapsules. However, this practice can lead to a reduction in the loading capacity of the microcapsule.

Another approach to improve microcapsules has been to create so-called "multi-core" microcapsules. For example, U.S. Pat. No. 5,780,056 discloses a "multi-core" microcapsule having gelatin as a shell material. These microcapsules are formed by spray cooling an aqueous emulsion of oil or carotenoid particles such that the gelatin hardens around "cores" of the oil or carotenoid particles. Yoshida et al. (Chemical Abstract 1990:140735 or Japanese Patent Publication JP 01-148338) discloses a complex coacervation process for the manufacture of microcapsules in which an emulsion of gelatin and paraffin wax is added to an arabic rubber solution and then mixed with a surfactant to form "multi-core" microcapsules. Ijichi et al. (*J. Chem. Eng. Jpn.* (1997) 30(5):793-798) microencapsulated large droplets of biphenyl using a complex coacervation process to form multi-layered microcapsules. U.S. Pat. Nos. 4,219,439 and 4,222,891 disclose "multi-nucleus" oil-containing microcapsules having an average diameter of 3-20 µm with an oil droplet size of 1-10 µm for use in pressure-sensitive copying papers and heat sensitive recording papers. While some improvement in the strength of microcapsules may be realized by using methods such as these, there remains a need for microcapsules having improved impermeability and good oxidative barrier to the encapsulated substance, preferably in conjunction with high load volumes. Disclosed herein are compositions and methods which meet these and other needs.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to microcapsules and methods for preparing and using them, as well as methods for improving various properties of microcapsules like impermeability.

Additional advantages will be set forth in part in the description that follows, and in part will be obvious from the description, or may be learned by practice of the aspects described below. The advantages described below will be realized and attained by means of the elements and combinations particularly, pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1a shows a cross-linking reaction between lysine and glutamine residues. FIG. 1b shows an acyl-transfer reaction. FIG. 1c shows a deamidation reaction. FIG. 1d is a schematic of a crosslinking reaction between two gelatin molecule chains by transglutaminase.

FIG. 6A is a micrograph of agglomerated multicore fish oil particles before the addition of $CoQ_{10}$ emulsion with a loading of 100 mg $CoQ_{10}$/500 mg EPA/DHA. FIG. 6B is a micrograph of the $CoQ_{10}$-coated multicore fish oil particles (with a loading of 100 mg $CoQ_{10}$/500 mg EPA/DHA). FIG. 6C is a micrograph of the finished $CoQ_{10}$-coated microcapsules (with a loading of 100 mg $CoQ_{10}$/500 mg EPA/DHA).

FIG. 7A is a micrograph of the agglomerated multicore fish oil particles before the addition of $CoQ_{10}$ emulsion with a loading of 30 mg $CoQ_{10}$/500 mg EPA/DHA. FIG. 7B is a micrograph of the $CoQ_{10}$-coated multicore fish oil particles (with a loading of 30 mg $CoQ_{10}$/500 mg EPA/DHA).

DETAILED DESCRIPTION

Figure 1:
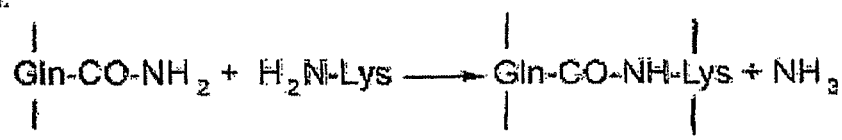
FIG. 1 is a schematic of reactions catalyzed by transglutaminase. Specifically.
Figure 1:
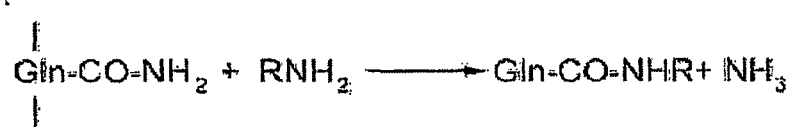
Figure 1:
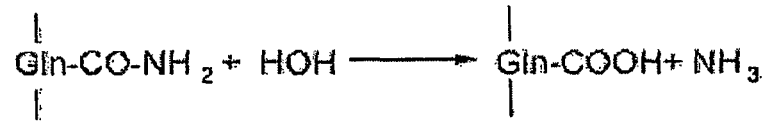
Figure 1:
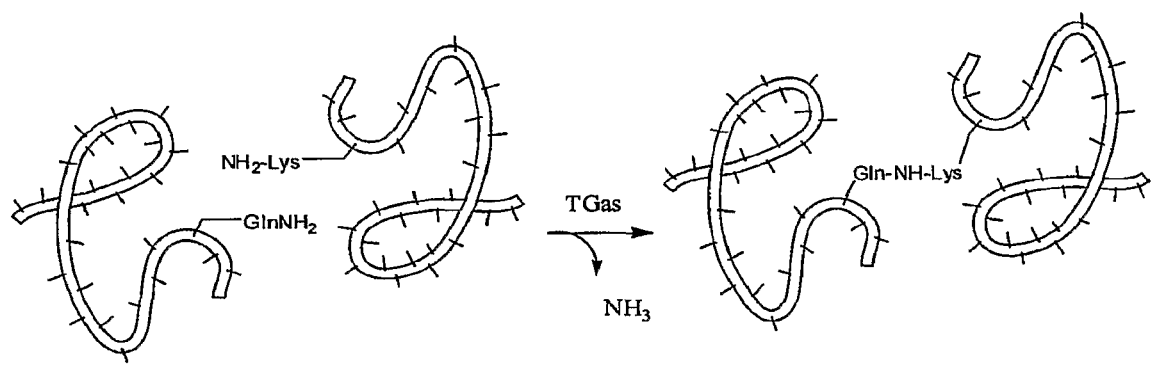

The materials, compounds, compositions, and methods described herein may be understood more readily by reference to the following detailed description of specific aspects of the disclosed subject matter and the Examples included therein and to the Figures.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an omega-3 fatty acid" includes mixtures of two or more such acids, reference to "the microcapsule" includes mixtures of two or more such microcapsule, and the like.

"Optional" or "optionally" means that the subsequently described event or circumstance can or cannot occur, and that the description includes instances where the event or circumstance occurs and instances where it does not. For example the phrase "adding a loading substance, a second polymer component, and, optionally, the composition, to the emulsion" includes instances where the composition is added to the emulsion and instances where the composition is not added to the emulsion.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular component in a composition denotes the weight relationship between the component and any other components in the composition for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

"Subject," as used herein, means an individual. In one aspect, the subject is a mammal such as a primate, and, in another aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

Reference will now be made in detail to specific aspects of the disclosed materials, compounds, compositions, articles, and methods, examples of which are illustrated in the accompanying Examples.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Microcapsules

The shells of many microcapsules, e.g., microcapsules with gelatin shells, are often "porous," which can allow oxygen in air or dissolved in water to diffuse into the loading substance core(s). Oxidation of the loading substance can cause stability and sensory problems. To overcome these problems, disclosed herein are microcapsules with improved shells and methods for preparing them. In general, disclosed are methods for preparing microcapsules that involve the use of waxes, saccharides, proteins, and small molecules such as amino acids and sugars to block the pores of a microcapsule shell and/or to increase the number of crosslinks in a microcapsule shell. Thus, the microcapsules disclosed herein generally have a combination of structural strength, impermeability, and high payload.

In certain aspects, disclosed herein are microcapsules that comprise an agglomeration of primary microcapsules and a loading substance, each individual primary microcapsule having a primary shell, wherein the loading substance is encapsulated by the primary shell and the agglomeration is encapsulated by an outer shell. These microcapsules are referred to herein as "multicore microcapsules." Also disclosed are "single-core" microcapsules that comprise a core, wherein the core comprises a loading substance, a primary shell surrounding the core, and an outer shell surrounding the primary shell. Unless stated otherwise, the term "microcapsule" is used herein to refer to multicore, single-core, or a mixture of multicore and single-core microcapsules. In these microcapsules (and others disclosed herein) the primary shell, the outer shell, or both the primary and outer shells comprise a residue of one or more compositions comprising an amino acid, protein, saccharide, wax, or combination thereof.

The term "residue" as used herein refers to the moiety that is the resulting product of the specified chemical species in a particular reaction scheme or subsequent formulation or chemical product, regardless of whether the moiety is actually obtained from the specified chemical species. For example, an "amino acid residue" refers to the moiety which results when an amino acid participates in a particular reaction (e.g., the residue can be the product of an amino acid undergoing a transglutaminase catalyzed crosslinking reaction with another amino acid). In this case, the amino acid residue is "derived" from the amino acid. It is understood that this moiety can be obtained by a reaction with a species other than the specified amino acid, for example, by a reaction with a protein or peptide containing the amino acid, and the like. This concept applies to other chemical species disclosed herein, such as protein, saccharides like chitosan, lactose, and sucrose, and waxes. Thus, when such species undergo particular reactions or treatment (e.g., acid/base reactions, crosslinking reactions with other chemical species, and functional group transformations), they are referred to herein as a residue of the corresponding chemical species.

It is also contemplated that one or more additional shell layers can be placed on the outer shell of the microcapsules. The techniques described in International Publication No. WO 2004/041251 A1, which is incorporated by reference in its entirety, can be used to add additional shell layers to the microcapsules.

As noted, the microcapsules disclosed herein can be such that the primary shell, the outer shell, or both the primary and outer shells comprise a residue of one or more compositions comprising an amino acid, protein, saccharide, wax, or combination thereof. This residue component can be different from the materials that make up the primary and/or outer shells. For example, if the primary and/or outer shell is made from a saccharide, and it is said that the primary and/or outer shells comprise a residue of a saccharide, then the disclosed microcapsules are such that the saccharide residue is different from the saccharides that are used to make the shell materials. Similarly, if the primary and/or outer shells are made from a protein, and it is said that the primary and/or outer shells comprise a residue of a protein, then the disclosed microcapsules are such that the protein residue is different from the protein that is used to make up the shell materials.

Induction Period

In many examples of microcapsules disclosed herein, the microcapsules have a long induction period. Induction period is a measure of a microcapsule's impermeability. Induction period can be measured by placing a sample of a microcapsule (about 5 g) in a container (e.g., glass container) and then putting the container with the sample into an oxygen-pressurized metal bomb. The pressurized bomb can be at an initial pressure of 5 bars (500 kPa) at 65° C. The changes in pressure are then recorded over time. The inflection point is taken as the induction period. A commercially available instrument that can be used to measure induction period is an OXIPRES™ (Mikrolab Aarhus A/S; Hojbjerg, Denmark). Generally, a more stable powder has a longer induction period at a constant temperature.

Many of the microcapsules disclosed herein can have an induction period (all induction period results are obtained from measurement at 65° C., unless otherwise specified) of greater than about 40, 47, 50, 75, or 100 hours. For example, disclosed herein are microcapsules that have an induction period of greater than about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours, where any of the stated values can form an upper or lower endpoint of a range.

Shell Materials

A number of different polymers can be used to produce the shell layers of the disclosed single-core and multicore microcapsules. For example, the primary shell and/or outer shell material of the disclosed microcapsules can comprise a surfactant, gelatin, protein, polyphosphate, polysaccharide, or mixtures thereof. Further examples of suitable materials for the primary shell and/or outer shell include, but are not limited to, gelatin type A, gelatin type B, polyphosphate, gum arabic, alginate, chitosan, carrageenan, pectin, low-methoxyl-pectin, starch, modified starch, alpha-lactalbumin, beta-lactoglobumin, ovalbumin, polysorbiton, maltodextrin, cyclodextrin, cellulose, methyl cellulose, ethyl cellulose, hydropropylmethylcellulose, carboxymethylcellulose, milk protein, whey protein, soy protein, canola protein, albumin, chitin, polylactides, poly-lactide-co-glycolides, derivatized chitin, poly-lysine, kosher gelatin, non-kosher gelatin, Halal gelatin, and non-Halal gelatin, including combinations and mixtures thereof. It is also contemplated that derivatives of these polymers can be used as well. One specific type of primary shell and/or outer shell material that can be used in the disclosed microcapsules is fish gelatin or pork gelatin.

In many examples of suitable microcapsules, the primary shell and/or outer shell material can have a Bloom number of from about 0 to about 350. The Bloom number describes the gel strength formed at 10° C. with a 6.67% solution gelled for 17±1 hours. Determining the Bloom number of a substance can be accomplished by methods known in the art. It is contemplated that the primary shell and/or outer shell material can have a Bloom number of about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 60, 61, 62, 63, 64, 65, 66, 67, 68, 69, 70, 70, 71, 72, 73, 74, 75, 76, 77, 78, 79, 80, 80, 81, 82, 83, 84, 85, 86, 87, 88, 89, 90, 90, 91, 92, 93, 94, 95, 96, 97, 98, 99, 100, 100, 101, 102, 103, 104, 105, 106, 107, 108, 109, 110, 110, 111, 112, 113, 114, 115, 116, 117, 118, 119, 120, 120, 121, 122, 123, 124, 125, 126, 127, 128, 129, 130, 130, 131, 132, 133, 134, 135, 136, 137, 138, 139, 140, 140, 141, 142, 143, 144, 145, 146, 147, 148, 149, 150, 150, 151, 152, 153, 154, 155, 156, 157, 158, 159, 160, 160, 161, 162, 163, 164, 165, 166, 167, 168, 169, 170, 170, 171, 172, 173, 174, 175, 176, 177, 178, 179, 180, 180, 181, 182, 183, 184, 185, 186, 187, 188, 189, 190, 190, 191, 192, 193, 194, 195, 196, 197, 198, 199, 200, 200, 201, 202, 203, 204, 205, 206, 207, 208, 209, 210, 210, 211, 212, 213, 214, 215, 216, 217, 218, 219, 220, 220, 221, 222, 223, 224, 225, 226, 227, 228, 229, 230, 230, 231, 232, 233, 234, 235, 236, 237, 238, 239, 240, 240, 241, 242, 243, 244, 245, 246, 247, 248, 249, 250, 250, 251, 252, 253, 254, 255, 256, 257, 258, 259, 260, 260, 261, 262, 263, 264, 265, 266, 267, 268, 269, 270, 270, 271, 272, 273, 274, 275, 276, 277, 278, 279, 280, 280, 281, 282, 283, 284, 285, 286, 287, 288, 289, 290, 290, 291, 292, 293, 294, 295, 296, 297, 298, 299, 300, 300, 301, 302, 303, 304, 305, 306, 307, 308, 309, 310, 310, 311, 312, 313, 314, 315, 316, 317, 318, 319, 320, 320, 321, 322, 323, 324, 325, 326, 327, 328, 329, 330, 330, 331, 332, 333, 334, 335, 336, 337, 338, 339, 340, 340, 341, 342, 343, 344, 345, 346, 347, 348, 349, or 350, where any of the stated values can form an upper or lower end point where appropriate. In some specific examples the primary and/or outer shell material can have a Bloom number of from about 0 to about 50, and in other examples the primary and/or outer shell material can have a Bloom number of from about 51 to about 350. Still other specific examples include microcapsules comprising a primary shell and/or outer shell material having a Bloom number of about 0, about 210, about 220, or about 240. In one example, the microcapsule does not contain "low Bloom" gelatin, which is gelatin having a Bloom number less than 50.

The shell material can be a two-component system made from a mixture of different types of polymer components, and where a composition has been added to the system to improve impermeability. In other examples, the shell material can be a complex coacervate between two or more polymer components (e.g., gelatin A and polyphosphate). Component A can be gelatin type A, although other polymers like those mentioned above for the shell materials are also contemplated as component A. Component B can be gelatin type B, polyphosphate, gum arabic, alginate, chitosan, carrageenan, pectin, low-methoxyl-pectin, carboxymethyl-cellulose or a mixture thereof. Again other polymers like those disclosed above for the shell materials are also contemplated as component B. The molar ratio of component A:component B that is used depends on the type of components but is typically from about 1:5 to about 15:1. For example, when gelatin type A and polyphosphate are used as components A and B respectively, the molar ratio of component A:component B can be about 8:1 to about 12:1; when gelatin type A and gelatine type B are used as components A and B respectively, the molar ratio of component A:component B can be about 2:1 to about 1:2; and when gelatin type A and alginate are used as components A and B respectively, the molar ratio of component A:component B can be about 3:1 to about 5:1. In many of the disclosed microcapsules the primary shell and/or outer shell can comprise a complex coacervate. For example, the primary shell and/or outer shell can comprise a complex coacervate of gelatin and polyphosphate. Other examples include a complex coacervate of gelatin and alginate, gelatin and pectin, gelatin and gum arabic, gelatin and xanthan, gelatin and low methoxyl pectin, and gelatin and whey protein.

In the disclosed microcapsules the outer shell can have an average diameter of from about 1 μm to about 2,000 μm, from about 20 μm to about 1,000 μm, or from about 30 μm to about 80 μm. In further examples, the average diameter of the outer shell can be about 1, 10, 20, 30, 40, 50, 60, 70, 80, 90, 200, 300, 400, 500, 600, 700, 800, 900, 1000, 1200, 1300, 1400, 1500, 1600, 1700, 1800, 1900, or 2000 μm, where any of the stated values can form an upper or lower endpoint when appropriate.

The primary shells of the disclosed microcapsules can have an average diameter of from about 40 nm to about 10 μm or from about 0.1 μm to about 5 μm. In further examples, the average diameter of the primary shell can be about 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm, 2 μm, 3 μm, 4 μm, 5 μm, 6 μm, 7 μm, 8 μm, 9 μm, 10 μm, where any of the stated values can form an upper or lower endpoint when appropriate. Particle size can be measured using any typical equipment known in the art, for example, a Coulter LS230 Particle Size Analyzer, Miami, Fla., USA.

Additional Compositions

As disclosed herein, the microcapsules can have a shell(s) (primary and/or outer) that contains additional compositions to improve the impermeability of the microcapsule. These additional compositions can be incorporated into the shell(s) at different points along the microcapsule preparation process, as is discussed more fully herein. In general, the additional compositions can be associated with the shell(s) through physical, electrostatic, ionic, van der Waals, steric, or chemical interactions. For example, the additional composition can physically be trapped inside a pore present in a shell, thus blocking the pore. In another example, the additional composition can be chemically bonded to the shell material through a covalent bond (e.g., through an enzymatically catalyzed crosslinking reaction).

Some specific examples of additional compositions that can be present in a shell(s) (primary and/or outer) of the disclosed microcapsules include, but are not limited to, amino acids, peptides, proteins, saccharides (i.e., mono-, di-, oligo-, or polysaccharides), and waxes, including combinations thereof and residues thereof. To illustrate further, a polysaccharide chitosan can be present in the shells of the disclosed microcapsules and can participate in an enzymatically crosslinking reaction between the first and/or second polymer components that are used to produce the shell material. The chitosan, with its multiple crosslinking sites, can thus be chemically bonded to the other polymer components in the shell material and thereby increase the shell's impermeability. In other examples, a small molecule like an amino acid or sugar can be physically trapped, entangled, or even chemically bonded to the shell(s) of a microcapsule, thus acting to reinforce the shell and/or block any pores. Larger wax particles and proteins can also be incorporated into a microcapsule shell to strengthen, reinforce, and/or improve impermeability by blocking any pores.

It is also contemplated that any combination of such additional compositions can be used and can be present in the shell material of the disclosed microcapsules. That is, one or more amino acids, one or more proteins, one or more saccharides, or one or more waxes can be used. Further, one or more amino acids and proteins, one or more amino acids and saccharides, or one or more amino acids and waxes can be used. Still further, one or more proteins and saccharides, or one or more proteins and waxes can be used. Also, one or more saccharides and waxes can be used. In yet another example, one or more amino acids, proteins, and saccharides, one or more amino acids, proteins, and waxes, one or more proteins, saccharides and waxes, one or more amino acids, saccharides, and waxes can be used.

Specific examples of amino acids, including residues thereof, that can be used in the disclosed microcapsule shell(s) include the 20 naturally encountered amino acids which make up proteins and polypeptides. In addition, it further includes less typical constituents which are both naturally occurring, such as, but not limited to formylmethionine and selenocysteine, analogs of typically found amino acids, and mimetics of amino acids or amino acid functionalities. Also contemplated are polymers if amino acids such as polylysine. Non-limiting examples of these and other molecules are discussed herein. In many examples the additional composition comprises lysine, leucine, isoleucine, glutamine, methionine, tyrosine, phenylalanine, tyrosine, tryptophan, cysteine or any combination thereof. The amino acids can be present in the shell material at a ratio of from about 1:5 to about 5:1, (e.g., about 2:1) in comparison to the second polymer component. Further examples include microcapsules with an amino acid to second polymer component ratio of about 1:5, 1:4, 1:3, 1:2, 1:1, 2:1, 3:1, 4:1, and 5:1, where any ratio can form an upper or lower endpoint of a range of ratios.

Suitable proteins, which also include "peptides," are compounds composed of amino acids chemically bound together. In general, the amino acids are chemically bound together via amide linkages (—CONH—); however, the amino acids may be bound together by other chemical bonds known in the art. For example, the amino acids can be bound by amine linkages. It is also possible to use peptides and proteins linked to other molecules (e.g., conjugates). For example, carbohydrates (e.g., glycoproteins) can be linked to the protein or peptide. Such derivatives, variants, and analogs of peptides and proteins are contemplated herein within the meaning of the terms protein. Some specific proteins include, but are not limited to, milk protein, gelatin, whey protein isolate, whey protein concentrate, caseinate, soy protein, BSA, and other abumen, including mixtures thereof. The proteins can be present in the shell material at a ratio to the second polymer component of from about 1:1 to about 40:1 (e.g., about 28.5:1). Further examples include microcapsules with a protein to second polymer component ratio of about 1:1, 5:1, 10:1, 15:1, 20:1, 25:1, 30:1, 35:1, and 40:1, where any ratio can form an upper or lower endpoint of a range of ratios.

Also suitable are polymeric amines, which are olefin based polymers that contain one or more amine functional group. Many such polyamines can be obtained commercially or can be prepared by methods known in the art. Suitable examples of polyamines that can used as a first active substance in the disclosed cellulose/active substance composites include, but are not limited to, polyvinyl amine and polyalkyleneimines like polyethyleneimine.

Saccharides, including residues thereof, are also suitable compositions that can be present in the disclosed microcapsule shells. Specific examples include N-acetylglucosamine polymer, such as chitosan and chitin. Chitosan is a naturally occurring polymer found in many fungi. However, as a matter of convenience, chitosan is obtained from chitin, which (after cellulose) is the second most abundant natural polymer. Chitin is readily isolated from shellfish or insect exoskeletons, and is also found in mollusks and fungi. Chitin is a water-insoluble copolymer of N-acetyl-D-glucosamine and D-glucosamine, but the great preponderance of monomer units are N-acetyl-D-glucosamine residues. Chitosan is a copolymer of the same two monomer units, but the preponderance of monomer units are D-glucosamine residues. Since the D-glucosamine residues bear a basic amino function, they readily form salts with acids. Many of these salts are water soluble. Treatment of chitin with concentrated caustic at elevated temperature converts N-acetyl-D-glucosamine residues into D-glucosamine residues and thereby converts chitin into chitosan. There is a continuum of compositions possible between pure poly-N-acetyl-D-glucosamine and pure poly-D-glucosamine. These compositions are all within the skill of the art to prepare and are all suitable for the uses described herein.

Suitable acids for making the chitosan salts for use in the methods described herein are those acids that form water-soluble salts with chitosan. It is not necessary that the acid itself be water-soluble; however, such water-soluble acids can ease handling. Inorganic acids, which form water-soluble chitosan salts, include the halogen acids and nitric acid, but exclude sulfuric and phosphoric acids because they do not form water-soluble salts with chitosan. Organic acids are particularly suitable and include, but are not limited to, lactic acid, glycolic acid, glutamic acid, formic acid, acetic acid, and a mixture thereof. Either mono- or poly-functional carboxylic acids can also be used. They can be aliphatic or aromatic, so long as they form water-soluble salts with chitosan.

Other polysaccharides and residues thereof that are suitable saccharides for the disclosed microcapsules are maltodextrin (DE18, DE 21, DE40 etc.), modified starch (N-LOK), oligofructans, cyclodextrins (alpha-, beta- and gamma-cyclodextrins), carboxymethylcellulose, hydroxypropylmethylcellulose (HPMC) (Methocel), ethylcellulose (Ethocel), hydroxypropyl cellulose (HPC) (e.g., Klucel), cellulose ether (e.g., Benecel), agar, alginate, pectin, low-methoxyl-pectin, gum arabic, carrageenan, cellulose gum, dilutan gum, gellan gum, locus bean gum, welan gum, and xanthan gum.

Other suitable saccharides, including residues thereof, are monosaccharides such as glucose, fructose, galactose, arabinose, ribose, ribulose, xylose, mannose, and xylulose. Still further, suitable saccharides, including residues thereof, include disaccharides or trisaccharides where the saccharide exists in the form of a pyranose or furanose (6 or 5 member rings). Non-limiting examples of di- and tri-saccharides include sucrose, lactose, cellobiose, sorbose, cellotriose, trehalose, maltose, and raffinose and the like. Particularly useful forms of saccharides that can be used are maple syrup, honey, and corn syrup, which are safe and can add flavor to the microcapsules. Various saccharide derivatives such as xylitol, sorbitol, isomalt, and glucosamine are also suitable for use in the disclosed microcapsules.

The saccharides disclosed herein can be present in the shell material at a ratio to the total shell material (first and second polymer components) of from about 1:0.2 to about 1:5 or about 1:0.02 to 1:0.5 the ratio to the second polymer component (e.g., polyphosphate). Further examples include microcapsules with a saccharide to total polymer component ratio of about 1:0.2, 1:0.5, 1:1, 1:1.5, 1:2.0, 1:2.5, 1:3.0, 1:3.5, 1:4.0, 1:4.5, and 1:5.0, where any ratio can form an upper or lower endpoint of a range of ratios. Still further examples include microcapsules with a saccharide to second polymer component ratio of about 1:0.02, 1:0.05, 1:0.1, 1:0.15, 1:0.2, 1:0.25, 1:0.3, 1:0.35, 1:0.4, 1:0.45, and 1:0.5, where any ratio can form an upper or lower endpoint of a range of ratios.

A suitable wax that can be present in the disclosed microcapsules shells is carnauba wax, which can be present in a microemulsion form. Other suitable waxes include, but are not limited to, candelilla, cersines, (synthetic) Japan wax, orange peel wax, rice bran wax, shellac, paraffin, montan, microcrystalline wax, polyethylene, and beeswax. The wax can be present in the shell material at a ratio to the second polymer component of from 1:1 to about 1:10. (e.g., 1:6). Further examples include microcapsules with a wax to second polymer component ratio of about 1:1, 1:2, 1:3, 1:4, 1:5, 1:6, 1:7, 1:8, 1:9, and 1:10, where any ratio can form an upper or lower endpoint of a range of ratios.

Loading Substances

In the disclosed microcapsules, the loading substance can be any substance that one desires to be microencapsulated (e.g., a substance that one desired to be delivered to a subject). In many examples, a suitable loading substance is not entirely soluble in an aqueous mixture. The loading substance can be a solid, a hydrophobic liquid, or a mixture of a solid and a hydrophobic liquid. In many of the examples herein, the loading substance can comprise a long chain polyunsaturated fatty acid, specific examples of which are included below. Further, the loading substance can comprise a biologically active substance, a nutrient such as a nutritional supplement, a flavoring substance, a polyunsaturated fatty acid like an omega-3 fatty acid, a vitamin, a mineral, a carbohydrate, a steroid, a trace element, and/or a protein, and the like including mixtures and combinations thereof. In other examples, the loading substance can comprise microbial oil, algal oil (e.g., oil from a dinoflagellate such as *Crypthecodinium cohnii*), fungal oil (e.g., oil from *Thraustochytrium, Schizochytrium*, or a mixture thereof), and/or plant oil (e.g., flax, vegetables), including mixtures and combinations thereof. In other examples, the loading substance can be a pharmaceutical composition (e.g., a drug and/or an enzyme) or a flavor. The loading substance can also be a hydrophobic liquid, such as grease, oil or a mixture thereof. Typical oils can be fish oils, vegetable oils (e.g., canola, olive, corn, rapeseed), mineral oils, derivatives thereof or mixtures thereof. The loading substance can comprise a purified or partially purified oily substance such as a fatty acid, a triglyceride, or a mixture thereof.

In still other examples, a suitable loading substance can comprise marine oil, such as natural and refined and concentrated fish oil. Examples of suitable fish oils include, but are not limited to, Atlantic fish oil, Pacific fish oil, Mediterranean fish oil, light pressed fish oil, alkaline treated fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonid oil, and shark oil, including mixtures and combinations thereof. Non-alkaline treated fish oil is also a suitable loading substance. Other marine oils suitable for use herein include, but are not limited to, squid oil, cuttle fish oil, octopus oil, krill oil, seal oil, whale oil, and the like, including mixtures and combinations thereof. Any marine oil and combination of marine oil can be used in the disclosed delivery devices and in the disclosed food articles and methods.

Many of the microbial, algal, fungal, plant, and marine oils disclosed herein contain omega-3 fatty acids. As such, certain delivery devices disclosed herein can contain a loading substance that comprises an omega-3 fatty acid, an alkyl ester of an omega-3 fatty acid, a triglyceride ester of an omega-3 fatty acid, a phytosterol ester of an omega-3 fatty acid, and/or mixtures and combinations thereof. An omega-3 fatty acid is an unsaturated fatty acid that contains as its terminus $CH_3$—$CH_2$—$CH$=$CH$—. Generally, an omega-3 fatty acid has the following formula:

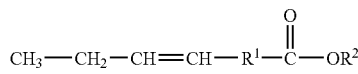

wherein $R^1$ is a $C_3$-$C_{40}$ alkyl or alkenyl group comprising at least one double bond and $R^2$ is H or alkyl group. The term "alkane" or "alkyl" as used herein is a saturated hydrocarbon group (e.g., methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like). The term "alkene" or "alkenyl" as used herein is a hydrocarbon group containing at least one carbon-carbon double bond. Asymmetric structures such as (AB)C=C(CD) are intended to include both the E and Z isomers (cis and trans). In a further example, $R^1$ can be a $C_5$-$C_{38}$, $C_6$-$C_{36}$, $C_8$-$C_{34}$, $C_{10}$-$C_{32}$, $C_{12}$-$C_{30}$, $C_{14}$-$C_{28}$, $C_{16}$-$C_{26}$, or $C_{18}$-$C_{24}$ alkenyl group. In yet another example, the alkenyl group of $R^1$ can have from 2 to 6, from 3 to 6, from 4 to 6, or from 5 to 6 double bonds. Still further, the alkenyl group of $R^1$ can have from 1, 2, 3, 4, 5, or 6 double bonds, where any of the stated values can form an upper or lower endpoint as appropriate.

Specific examples of omega-3 fatty acids that are suitable loading substances that can be used in the disclosed delivery devices include, but are not limited to, α-linolenic acid (18:3ω3), octadecatetraenoic acid (18:4ω3), eicosapentaenoic acid (20:5ω3) (EPA), eicosatetraenoic acid (20:4ω3), henicosapentaenoic acid (21:5ω3), docosahexaenoic acid (22:6ω3) (DHA), docosapentaenoic acid (22:5ω3) (DPA), including derivatives and mixtures thereof. Many types of fatty acid derivatives are well known to one skilled in the art. Examples of suitable derivatives are esters, such as phytosterol esters, furanoid esters, branched or unbranched $C_1$-$C_{30}$ alkyl esters, branched or unbranched $C_2$-$C_{30}$ alkenyl esters or branched or unbranched $C_3$-$C_{30}$ cycloalkyl esters, in particular phytosterol esters and $C_1$-$C_6$ alkyl esters. In a further example, the loading substance can be a phytosterol ester of docosahexaenoic acid and/or eicosapentaenoic acid, a $C_1$-$C_6$ alkyl ester of docosahexaenoic acid and/or eicosapentaenoic acid, a triglyceride ester of docosahexaenoic acid and/or eicosapentaenoic acid, and/or a mixture thereof.

Other examples of suitable loading substances that can be present in the disclosed delivery devices comprise at least 4, at least 6, at least 8, at least 10, at least 12, at least 14, at least 16, at least 18, or at least 20 carbon atoms. In some other examples, the loading substance can contain about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. In still other examples, the loading substance can comprise a mixture of fatty acids (including derivatives thereof) having a range of carbon atoms. For example, the loading substance can comprise from about 8 to about 40, from about 10 to about 38, from about 12 to about 36, from about 14 to about 34, from about 16 to about 32, from about 18 to about 30, or from about 20 to about 28 carbon atoms.

Some further examples of loading substances are those that contain at least one unsaturated bond (i.e., a carbon-carbon double or triple bond). For example, the loading substance can contain at least 2, at least 3, at least 4, at least 5, at least 6, at least 7, or at least 8 carbon-carbon double bonds, triple bonds, or any combination thereof. In another example, the loading substance can comprise 1, 2, 3, 4, 5, 6, 7, or 8 unsaturated bonds, where any of the stated values can form an upper or lower endpoint as appropriate.

Some specific examples of loading substances, which are unsaturated fatty acids, are shown in the following tables. Derivatives of these fatty acids are also suitable and are thus contemplated herein.

TABLE 1

Examples of Monoene Acids

| Total number of carbon atoms in the fatty acid chain | Carbon number where double bond begins. ("c" denotes a cis double bond; "t" denotes a trans double bond) |
|---|---|
| 10 | 4c |
| 12 | 4c |
| 14 | 4c and 9c |
| 16 | 3t, 4c, 5t, 6c, 6t, 9c (palmitooleic), and 11c |
| 18 | 3t, 5c, 5t, 6c (petroselinic), 6t, 9c (oleic), 10c, 11c (cis-vaccenic), 11t (vaccenic), and 13c |
| 20 | 5c, 9c (gadolenic), 11c; 13c, and 15c |
| 22 | 5c, 11c (cetoleic), 13c (erucic), and 15c |
| 24 | 15c (selacholeic, nervonic) |
| 26 | 9c, and 17c (ximenic) |
| 28 | 9c, 19c (lumequic) |
| 30 | 21c |

Unsaturated fatty acids that contain at least one pair of methylene interrupted unsaturated bonds are also suitable loading substances. By "methylene interrupted unsaturated bond" is meant that one carbon-carbon double or triple bond is separated from another carbon-carbon double or triple bond by at least one methylene group (i.e., $CH_2$). Specific examples of such loading substances include, but are not limited to, the n−1 family derived from 9, 12, 15-16:3; n−2 family derived from 9, 12, 15-17:3, 15:3, 17:3, 17:4, 20:4; n−3 family derived from 9, 12, 15-18:3, 15:2, 15:3, 15:4, 16:3, 16:4, 18:3 (α-linolenic), 18:4, 18:5, 20:2, 20:3, 20:4; 20:5 (EPA), 21:5, 22:3, 22:5 (DPA), 22:6 (DHA), 24:3, 24:4, 24:5, 24:6, 26:5, 26:6, 28:7, 30:5; n−4 family derived from 9, 12-16:2, 16:2, 16:3, 18:2, 18:3; n−5 family derived from 9, 12-17:2, 15:2, 17:2, 17:3, 19:2, 19:4, 20:3, 20:4 21:4, 21:5; n−6 family derived from 9, 12-18:2, 15:2, 16:2, 18:2 (linoleic acid), 18:3 (γ-linolenic acid); 20:2, 20:3, 20:4 (arachidonic acid), 22:2, 22:3, 22:4 (adrenic acid), 22:5, 24:2, 24:4, 25:2, 26:2, 30:4; n−7 family derived from 9-16:1, 15:2, 16:2, 17:2, 18:2, 19:2; n−8 family derived from 9-17:1, 15:2, 16:2, 17:2, 18:2, 19:2; n−9 family derived from 9-18:1, 17:2, 18:2, 20:2, 20:3, 22:3, 22:4; n−11 family 19:2, and the n−12 family 20:2. In one particular specific example, the loading substance can comprise arachidonic acid.

In the above paragraph (and throughout) the compounds are identified by referring first to the "n-x family," where x is the position in the fatty acid where the first double bond begins. The numbering scheme begins at the terminal end of the fatty acid, where, for example, the terminal $CH_3$ group is designated position 1. In this sense, the n−3 family would be an omega-3 fatty acid, as described above. The next number identifies the total number of carbon atoms in the fatty acid. The third number, which is after the colon, designates the total number of double bonds in the fatty acid. So, for example, in the n−1 family, 16:3, refers to a 16 carbon long fatty acid with 3 double bonds, each separated by a methylene, wherein the first double bond begins at position 1, i.e., the terminal end of the fatty acid. In another example, in the n−6 family, 18:3, refers to an 18 carbon long fatty acid with 3 methylene separated double bonds beginning at position 6, i.e., the sixth carbon from the terminal end of the fatty acid, and so forth.

Further examples of loading substances that contain at least one pair of methylene interrupted unsaturated bonds are shown in Table 2.

TABLE 2

Examples of Polyene Acids

| Total number of carbon atoms in the fatty acid chain | Carbon number where double bond begins. ("c" denotes a cis double bond; "t" denotes a trans double bond) |
|---|---|
| 18 | 5, 9 |
|  | 5, 11 |
|  | 2t, 9, 12 |
|  | 3t, 9, 12 |
|  | 5t, 9, 12 |
|  | 5, 9, 12 |
|  | 5, 11, 14 |
|  | 3t, 9, 12, 15 |
|  | 5, 9, 12, 15 |
| 20 | 5, 11 |
|  | 5, 13 |
|  | 7, 11 |
|  | 7, 13 |
|  | 5, 11, 14 |
|  | 7, 11, 14 |
|  | 5, 11, 14, 17 |
| 22 | 5, 11 |
|  | 5, 13 |
|  | 7, 13 |
|  | 7, 15 |
|  | 7, 17 |
|  | 9, 13 |
|  | 9, 15 |

Specific examples of suitable loading substances that contain conjugated unsaturated bonds include, but are not limited to, those in Table 3. By "conjugated unsaturated bond" is meant that at least one pair of carbon-carbon double and/or triple bonds are bonded together, without a methylene ($CH_2$) group between them (e.g., —CH=CH—CH=CH—).

TABLE 3

Examples of Conjugated Polyene Acids

| Total number of carbon atoms in the fatty acid chain. | Carbon number where double bond begins. ("c" denotes a cis double bond; "t" denotes a trans double bond) |
|---|---|
| 10 | 2t, 4t, 6c |
|  | 2c, 4t, 6t |
|  | 3t, 5t, 7c |
|  | 3c, 5t, 7t |
| 12 | 3, 5, 7, 9, 11 |
| 14 | 3, 5, 7, 9, 11 |
| 18 | 10t, 12t |
|  | 8c, 10t, 12c (jacaric) |
|  | 8t, 10t, 12c (calendic) |
|  | 8t, 10t, 12t |
|  | 9t, 11t, 13c (catalpic) |
|  | 9c, 11t, 13t (α-eleostearic) |
|  | 9c, 11t, 13c (punicic) |
|  | 9t, 11t, 13t (β-eleostearic) |
|  | 9c, 11t, 13t, 15c (α-parinaric) |
|  | 9t 11t, 13t, 15t (β-parinaric) |

In the above examples of suitable loading substances, derivatives of the disclosed loading substances can also be used. By "derivatives" is meant the ester of a fatty acid (e.g., methyl and ethyl esters), salts of the fatty acids (e.g., sodium and potassium salts), and triglycerides, diglycerides, and monoglycerides, sterol esters, antioxidant-oil conjugates (e.g., ascorbyl palmitate), and naturally derivatives such as furanoid fatty acid derivatives.

The loading substances disclosed herein can also be crude oils, semi-refined (also called alkaline refined), or refined oils from such sources disclosed herein. Still further, the disclosed compositions and methods can use oils comprising re-esterified triglycerides.

It is contemplated herein that one or more of the disclosed loading substances can be used. For example the disclosed delivery devices can contain two or more different loading substances. Further, the loading substance can be present in an amount of from about 1% to about 50% by weight of a microcapsule. In specific examples, the loading substance can be present in an amount of from about 1% to about 40%, from about 1% to about 30%, from about 1% to about 20%, from about 1% to about 15%, or from about 1% to about 10% by weight of a microcapsule.

In one example, the loading substance is not a fatty acid conjugate. A fatty acid conjugate is a fatty acid that has been coupled to (e.g., bonded to) another chemical moiety, such as a metal (e.g., chromium) or cofactor ($CoQ_{10}$). In other examples, the loading substance is not an oil with a low interfacial tension (IT) (i.e., having an interfacial tension of less than about 15 dynes/cm). In other examples, the loading substance is such a fatty acid conjugate or low IT oil.

In one example, the loading substances can be or can contain an antioxidant. Suitable examples of antioxidants include, but are not limited to, a phenolic compound, a plant extract, or a sulfur-containing compound. In certain examples disclosed herein the antioxidant can be ascorbic acid or a salt thereof, e.g., sodium ascorbate. In other examples, the antioxidant can be citric acid or a salt thereof. In still other examples, the antioxidant can be vitamin E, $CoQ_{10}$, lutein, zeaxanthan, carotene (e.g., beta-carotene) tocopherols, lipid soluble derivatives of more polar antioxidants such as ascorbyl fatty acid esters (e.g., ascorbyl palmitate), plant extracts (e.g., rosemary, sage and oregano oils), algal extracts, and synthetic antioxidants (e.g., BHT, TBHQ, ethoxyquin, alkyl gallates, hydroquinones, tocotrienols), or mixtures thereof.

The disclosed loading substance can also be or can contain other nutrient(s) such as vitamins other trace elements (e.g., zinc), minerals, and the like. Further, the loading substances can comprise other components such as preservatives, antimicrobials, anti-oxidants, chelating agents, thickeners, flavorings, diluents, emulsifiers, dispersing aids, or binders, including any mixture thereof.

In addition, the loading substance can have a low interfacial tension. For example, a suitable loading substance can have an interfacial tension of less than about 20, less than about 15, less than about 11, less than about 9, less than about 7, or less than about 5 dynes/cm. In other examples, the loading substance can have an interfacial tension of from about 0.1 to about 20, from about 1 to about 15, from about 2 to about 9, from about 3 to about 9, from about 4 to about 9, from about 5 to about 9, or from about 2 to about 7 dynes/cm. In still further examples, the loading substance can have an interfacial tension of about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0, where any of the stated values can form an upper or lower endpoint when appropriate. In particular examples, the loading substance can be an algal oil with an interfacial tension of about 0.5, 0.6, 0.7, 0.8, 0.9, or 1.0 dynes/cm. The loading substance can also be a fungal oil with an interfacial tension of about 3.0, 3.1, 3.2, 3.3, or 3.4 dynes/cm.

The interfacial tension of a loading substance can be determined by methods known in the art. For example, the interfacial tension from a loading substance to a standard gelatin solution or from a loading substance to distilled water can be determined with a Fisher Surface Tensiomat. Generally, a standard gelatin solution or distilled water can be poured into a sample vessel, which is placed on the sample table of a tensiomat. The loading substance can then be added to the sample vessel. The sample can be raised so that the ring of the tensiomat is immersed in the loading substance. The interfacial tension is the measure of downward force on the ring as it passes through the interface of the loading substance and standard gelatin solution or the interface of the loading substance and distilled water, depending on whichever experimental setup is being used.

The interfacial tension measurements disclosed herein for the loading substances refer to values determined as just described using a standard gelatin solution (50° C.) that contains 3.3% (w/w) of 240 Bloom kosher fish gelatin (e.g., from LAPI, Tuscany, Italy), 0.5% (w/w) sodium ascorbate, and 0.33% (w/w) polyphosphate solution dissolved in distilled water.

Further, the payloads of loading substances in the disclosed microcapsules can be from about 20% to about 90%, about 50% to about 70% by weight, or about 60% by weight of the microcapsule. In other examples, the disclosed microcapsules can contain about 20, 25, 30, 35, 40, 45, 50, 55, 60, 65, 70, 75, 80, 85, or 90% by weight of the microcapsule, where any of the stated values can form an upper or lower endpoint when appropriate.

Specific Examples

Specific examples of microcapsules that contain any of the shell materials and any of the loading substances are disclosed herein. Some specific examples include, but are not limited to, microcapsules where the shell materials are complex coacervates, e.g., coacervates of gelatin and polyphosphate. The shell material can, in certain examples, comprise gelatin with a Bloom number of from about 0 to about 50. Loading substances that can be used can, in many instances, include marine oils (e.g., fish oils and algal oils). Loading substances that comprise omega-3 fatty acids such as EPA and DHA can also be desirable. Further, derivatives of omega-3 fatty acids, such as mono-, di-, and triglycerides, alkyl esters, sterol esters, antioxidant esters (e.g., ascorbyl and citryl esters), and furanoid esters, can also be suitable loading substances.

Some particularly suitable microcapsules include microcapsules containing fish oils. Examples of such fish oils include, but are not limited to, sardine, anchovy, bonito, and/or tuna oil. Fish oils can also be referred to herein by the approximate ratio of EPA and DHA, or derivatives thereof, found in the oil. For example, 18:12 oils generally comprise a ratio of EPA to DHA (or their triglyceride esters for example) of about 18:12. Likewise, 5:25 oils generally comprise a ratio of EPA to DHA of about 5:25. Any of these oils can be encapsulated in a complex coacervate comprising and fish or pork gelatin. Such microcapsules can be Generally Regarded as Safe (GRAS), kosher, and/or Halal. Also, such microcapsules can have at least about 130 mg of DHA or at least about 150 mg of EPA and DHA per gram of powder. Further, antioxidants such as ascorbic acid, citric acid, and/or phosphoric acid (or salts thereof) can be present in such microcapsules.

Some specific examples of food articles disclosed herein comprise microcapsules having about 130 mg of DHA per gram of microcapsule (e.g., a microcapsule wherein the loading substance comprises a 5:25 oil derived from tuna and/or bonito) and the outer shell of the microcapsules comprises pork or fish gelatin. In another specific example, a food article disclosed herein can comprise a microcapsule having about 150 mg of DHA and EPA per gram of microcapsule (e.g., a microcapsule wherein the loading substance comprises a 18:12 oil derived from sardine and/or anchovy) and the outer shell of the microcapsules comprises pork or fish gelatin.

Particularly suitable microcapsules are disclosed in U.S. Pat. Nos. 6,974,592 and 6,969,530 and US Publication No. 2005-0019416-A1, which are all incorporated by reference herein in their entireties for at least their disclosures of microcapsules, their methods of preparation, and their methods of use.

Method of Making Microcapsules

Microcapsules prepared by the processes disclosed herein typically have a combination of payload and structural strength that are suitable for food articles, supplements, formulation vehicles, and methods disclosed herein. In one example, the methods disclosed in U.S. Pat. Nos. 6,974,592 and 6,969,530, and US Publication No. 2005-0019416-A1, which are incorporated by reference in their entirety, can be used to prepare microcapsules. It is also contemplated that one or more additional shell layers can be placed on the outer shell of the single-core or multicore microcapsules. In one example, the techniques described in International Publication No. WO 2004/041251 A1, which is incorporated by reference in its entirety, can be used to add additional shell layers to the single-core and multicore microcapsules.

In general, suitable microcapsules can be prepared by a process that comprises providing an emulsion comprising a first polymer component and a loading substance; adding a second polymer component to the emulsion; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; and further cooling the aqueous mixture to form an outer shell around the agglomeration.

In these methods, the first polymer component and second polymer component can be the same as any of the primary and outer shell materials described herein. That is, the first and second polymer components can become the primary and/or outer shell materials in the disclosed methods for preparing microcapsules. Furthermore, any of the loading substances described herein can be used in these methods for preparing microcapsules.

In the disclosed methods, an aqueous mixture of a loading substance, a first polymer component of the shell material, and a second polymer component of the shell material is formed. The aqueous mixture can be a mechanical mixture, a suspension, or an emulsion. When a liquid loading substance is used, particularly a hydrophobic liquid, the aqueous mixture can be an emulsion of the loading substance and the polymer components. In another example, a first polymer component is provided in aqueous solution, together with processing aids, such as antioxidants. A loading substance can then be dispersed into the aqueous mixture, for example, by using a homogenizer. If the loading substance is a hydrophobic liquid, an emulsion is formed in which a fraction of the first polymer component begins to deposit around individual droplets of loading substance to begin the formation of primary shells. If the loading substance is a solid particle, a suspension is formed in which a fraction of the first polymer component begins to deposit around individual particles to begin the formation of primary shells. At this point, another aqueous solution of a second polymer component can be added to the aqueous mixture.

In the processes for preparing microcapsules disclosed herein, providing an emulsion of the first polymer component and the loading substance can be accomplished by methods and apparatus known in the art, e.g., homogenization and high pressure/high shear pumps. For example, emulsification can take place by emulsifying at from about 1,000 to about 15,000 rpm. The emulsification step can be monitored by removing a sample of the mixture and analyzing it under such methods as microscopy, light scattering, turbidity, etc. Generally, emulsification can be performed until an average droplet size of less than about 1,000, 750, 500, 100, or 10 nm is obtained. Not wishing to be bound by theory but it is believed that by varying the emulsification speed it is possible to produce single or multicore microcapsules. For example, when lower emulsification speeds are used (e.g., 1,000 to 2,000 rpm), the droplets of the loading substance are large enough to form a single particle, which upon encapsulation, produces a single core microcapsule. Conversely, if high emulsification speeds are used (e.g., 5,000 to 15,000 rpm), the resultant droplets of loading substance are usually small (e.g., from 1 to 10 μm). These tiny droplets can have higher surface energy and can readily form agglomerations when pH and/or temperature is adjusted accordingly, which results in the formation of multicore microcapsules upon encapsulation. Particle size can be measured using any typical equipment known in the art, for example, a COULTER™ LS230 Particle Size Analyzer, Miami, Fla. USA.

The emulsification step can be performed at greater than room temperature, greater than 30, 40, 50, 60, 70, or 80° C., where any of the stated values can form an upper or lower endpoint when appropriate. Specific examples include emulsifying the mixture at from about 30° C. to about 60° C. or from about 40° C. to about 50° C.

It is further contemplated that antioxidants and/or surfactants, which are also described herein, can be added to the emulsion and/or aqueous mixture. Such antioxidants and/or surfactants can be added before, during, and/or after the emulsion is provided. Further, in the whole system involving the loading substance, shell materials, antioxidants, and additional compositions, the antioxidative capacity is at a certain level when the amount of antioxidants used is given. Therefore, in the methods for preparing microcapsules disclosed herein, purging with inert gas such as nitrogen during any or all of emulsification, mixing, coacervation, and or cooling processes can prevent the consumption of antioxidants by oxygen from air, and delay oxidation of the loading substance during storage. It can also prevent the formation of off-flavor compounds due to oxidation in the microencapsulation process.

Also contemplated is that chelators can be added to the emulsion and/or aqueous mixture. Autoxidation of lipids is catalyzed by metal ions, particularly iron and copper ions. Thus, chelating of the metal ions can help retard the oxidation and extend its "lag phase," therefore extending the shelf-life of bulk oil or encapsulated oils. Like antioxidants, the chelators can be added before, during and/or after the emulsion is provided. Examples of suitable chelators include, but are not limited to are disodium ethylenediamine tetraacetic acid, which is one of the most frequently used chelating agents in food processing, citric acid, phytic acid, malic acid, tartaric acid, oxalic acid, succinic acid, polyphosphoric acids etc.

The amount of the polymer components of the shell material provided in the aqueous mixture is typically sufficient to form both the primary shells and the outer shells of the loading agglomeration of microcapsules. The loading substance can be provided in an amount of from about 1% to about 15% by weight of the aqueous mixture, from about 3% to about 8% by weight, or about 6% by weight.

The pH, temperature, concentration, mixing speed, or a combination thereof can be adjusted to form an aqueous mixture comprising a primary shell material, wherein the primary shell material comprises the first and second polymer components and surrounds the loading substance. If there is more than one type of polymer component, complex coacervation will occur between the components to form a coacervate, which further deposits around the loading substance to form primary shells of shell material. The pH adjustment depends on the type of shell material to be formed. For example, the pH may be adjusted to a value from 3.5 to 5.0, or from 4.0 to 5.0. If the pH of the mixture starts in the desired range, then little or no pH adjustment is required.

The initial temperature of the aqueous mixture can be from about 20° C. to about 60° C., or about 30° C. to about 50° C.

Mixing can be adjusted so that there is good mixing without breaking the microcapsules as they form. Particular mixing parameters depend on the type of equipment being used. Any of a variety of types of mixing equipment known in the art may be used. In one example, an axial flow impeller, such as LIGHTNIN™ A310 or A510, can be used.

In many examples disclosed herein, the primary shell and the outer shell of the disclosed microcapsules can comprise a complex coacervate. The complex coacervate can be formed from the first and second polymer components. For example, the primary shell and the outer shell can comprise a complex coacervate between gelatin and polyphosphate. All combinations of first and second polymer components are contemplated herein for the complex coacervate and the primary and outer shell.

The aqueous mixture can then be cooled under controlled cooling rate and mixing parameters to permit agglomeration of the primary shells to form encapsulated agglomerations of primary shells. Not wishing to be bound by theory, the encapsulated agglomerations are discrete particles themselves. It is advantageous to control the formation of the encapsulated agglomerations at a temperature above the gel point of the shell material, and to let excess shell material form a thicker outer shell. It is also possible at this stage to add more polymer, where the polymer is the same or different as the shell material being used, in order to thicken the outer shell and/or produce microcapsules having primary and outer shells of different composition. The outer shell encapsulates the agglomeration of primary shells to form a rigid encapsulated agglomeration of microcapsules.

Cooling the aqueous mixture can be accomplished by methods known in the art (e.g., the use of a chiller). The rate of cooling can be about 1° C. per about 1 to about 100 minutes. For example, the rate of cooling can be about 1° C. per about 1, 5, 10, 15, 20, 25, 30, 35, 40, 45, 50, 55, 60, 65, 70, 75, 80, 85, 90, 95, or 100 minutes, where any of the stated values can form an upper or lower endpoint when appropriate. In specific examples the rate of cooling can be about 1° C./5 minutes. Cooling can take place until the mixture reaches a temperature of from about 5° C. to about 10° C., e.g., about 5° C.

Processing aids can be included in the shell material (e.g., primary and/or outer shells). Processing aids can be used for a variety of reasons. For example, they may be used to promote agglomeration of the primary microcapsules, stabilize the emulsion system, improve the properties of the outer shells, control microcapsule size, and/or to act as an antioxidant. In one aspect, the processing aid can be an emulsifier, a fatty acid, a lipid, a wax, a microbial cell (e.g., yeast cell lines), a clay, or an inorganic compound (e.g., calcium carbonate). Not wishing to be bound by theory, these processing aids can improve the barrier properties of the microcapsules. In one aspect, one or more antioxidants can be added to the shell material. Antioxidant properties are useful both during the process (e.g., during coacervation and/or spray drying) and in the microcapsules after they are formed (i.e., to extend shelf-life, etc). Preferably a small number of processing aids that perform a large number of functions can be used. In one aspect, the antioxidant can be a phenolic compound, a plant extract, or a sulfur-containing amino acid. In one aspect, ascorbic acid or citric acid (or a salt thereof such as sodium or potassium ascorbate or sodium or potassium citrate) can be used to promote agglomeration of the primary microcapsules, to control microcapsule size and to act as an antioxidant. The antioxidant can be used in an amount of about 100 ppm to about 12,000 ppm, or from about 1,000 ppm to about 5,000 ppm. Other processing aids such as, for example, metal chelators, can be used as well. For example, ethylene diamine tetraacetic acid can be used to bind metal ions, which can reduce the catalytic oxidation of the loading substance.

In the disclosed microcapsules, the shell material can also be cross-linked. Thus, the disclosed methods can further involve the addition of a cross-linker. The cross-linker can be added to further increase the rigidity of the microcapsules by cross-linking the shell material in both the outer and primary shells and to make the shells insoluble in both aqueous and oily media. In one example, the cross-linker is added after the outer shell of the microcapsule is produced. Any suitable cross-linker can be used and the choice of cross-linker can vary depending upon the selection of the first and second polymer component. In another example, the cross-linkers can be enzymatic cross-linkers (e.g. transglutaminase), aldehydes (e.g. formaldehyde or glutaraldehyde), tannic acid, alum or a mixture thereof. In another aspect, the cross-linker can be a plant extract or a phenolic. It is also contemplated that one or more loading substances (e.g., antioxidants) can be used with the cross-linker. When the microcapsules are to be used in a formulation that is to be delivered to an organism, the cross-linkers are preferably non-toxic or of sufficiently low toxicity. The amount of cross-linker used depends on the components selected and can be adjusted to provide more or less structural rigidity as desired. In one aspect, the amount of cross-linker that can be used is in the amount of about 0.1% to about 5.0%, about 0.5% to about 5.0%, about 1.0% to about 5.0%, about 2.0% to about 4.0%, or about 2.5%, by weight of the first polymer component. In general, one skilled in the art can routinely determine the desired amount in any given case by simple experimentation. The cross-linker can be added at any stage of the process; however, it can typically be added after the cooling step.

Further, in some applications, the use of transglutaminase to crosslink the microcapsules may not be desired (e.g., the temperature and pH are too low and/or the transglutaminase is expensive). Thus, it is contemplated herein that the use of glutaraldehyde can be in the disclosed methods to cross-link the disclosed microcapsules. In certain examples, the use of one or more compositions comprising an amino acid or protein, can react with residual glutaraldehyde that was totally or partially unreacted from the crosslinking reaction. That is, unreacted and half reacted glutaraldehyde (i.e., with one aldehyde group still reactive) can be neutralized by the ε-amino group of lysine or other amino groups on proteins, making the final product safer. In this sense, the compositions comprising amino acids and/or proteins can improve the microcapsule shell by filling any pores and neutralize glutaraldehyde from the crosslinking reaction. This approach can also eliminate the need to wash the microcapsule after crosslinking since the microcapsule will be essentially free of glutaraldehyde. Crosslinking can also be accomplished with genipin (e.g., with genipin and carboxylmethyl chitosan).

Further, the disclosed microcapsules can be washed with water and/or dried to provide a free-flowing powder. Thus, the disclosed methods of preparing microcapsules can comprise a drying step for the microcapsules. Drying can be accomplished by a number of methods known in the art such as, for example, freeze drying, drying with ethanol, or spray drying. In one aspect, spray drying can be used for drying the microcapsules. Spray drying techniques are disclosed in "Spray Drying Handbook", K. Masters, 5th edition, Longman Scientific Technical UK, 1991, the disclosure of which is hereby incorporated by reference at least for its teaching of spray drying methods.

Adding Saccharides Before Coacervation

In certain examples, saccharides like the polysaccharide chitosan, chitin, and others disclosed herein can be added before emulsification and coacervation to provide microcapsules with improved impermeability. While not wishing to be bound by theory, the addition of saccharides to the polymer component (e.g., gelatin) solution increases the viscosity of the medium, and can therefore aid in the stabilization of the oil droplets after emulsification. To illustrate, the polysaccharide chitosan, being composed of D-glucosamine units, carries a great number of amine groups as shown below.

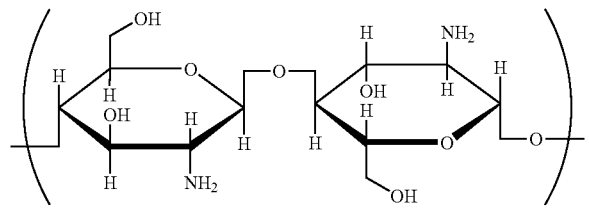

Thus, at certain pH, the cationic molecule will participate in the electrostatic interactions during coacervation. The chitosan will then form a "composite" shell material together with first and second polymer materials (e.g., the gelatin-polyphosphate coacervates).

Figure 2:
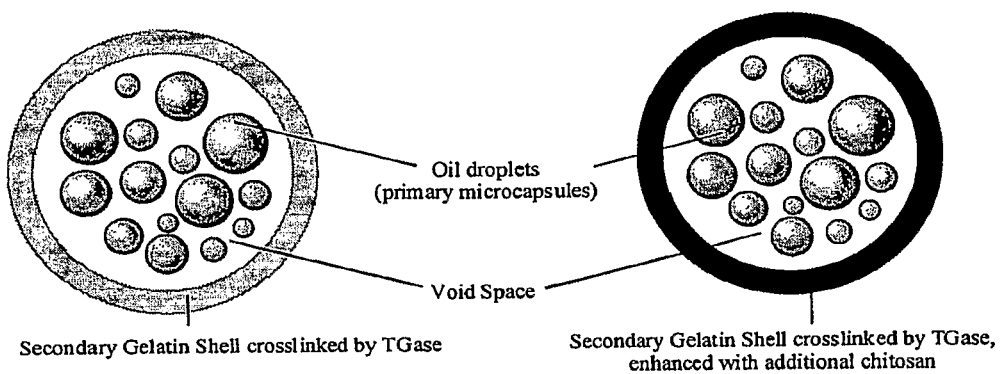
FIG. 2 is a pair of schematics of two multicore microcapsules, one where the secondary shell material of gelatin is crosslinked by transglutaminase and the other where the secondary (outer) shell material of gelatin with chitosan is crosslinked with transglutaminase.

Furthermore, transglutaminase (TGase) can crosslink proteins (i.e., gelatin) (FIG. 1), including gelatin incorporated with chitosan. While not all amine groups on lysine and glutamine residues on gelatin are crosslinked by TGase, incorporating saccharides like chitosan into the shell material can form extra crosslinks to form bridging between gelatin molecules. Therefore, the shell strength would be greater and the pore size can be reduced (thus, better oxygen barrier) (FIG. 2).

Adding Saccharides and/or Amino Acids after Shell Formation and Crosslinking

In another example, amino acids such as lysine and/or glutamine can be added to the microcapsules after they are formed, but before or after crosslinking with transglutaminase. As discussed above, to form crosslinks between the amine groups of lysine and glutamine, these two amino residues have to be in correct spatial position so that TGase can catalyze the reaction. It can be assumed that not all amine groups are able to form crosslinks. Therefore, after shell formation and crosslinking, there are amine groups on the gelatin shell material available. When lysine and glutamine are added, TGase will be able to attach them to glutamine and lysine residues on gelatin molecules, respectively. This can therefore form attachments of amino acids inside the pores of the shell, and can improve the barrier properties of the microcapsules.

A combination of polysaccharides like chitosan and amino acids can also be used. For examples, when chitosan is added after shell formation and crosslinking of the shell, it can attach onto lysine and glutamine residues, or form bridging between gelatin molecules or domains with lysine's available $NH_2$ moiety and/or glutamine's available $NH_2$ moiety.

When chitosan is added with lysine and glutamine, the effect can in certain circumstances be better as they can fit pores with different sizes.

In some circumstances, the use of lysine and glutamine can promote moisture sorption, which may not be desired. Thus, disclosed herein is the use of amino acids such as cysteine, leucine, isoleucine, phenylalanine, tyrosine, tryptophan, and tyrosine alone, in combination, or in combination with glutamine and/or chitosan. Such microcapsule powder can have better moisture barrier because these amino acids are more hydrophobic than lysine. Therefore, the caking of the powder can be slowed.

Adding Wax

Figure 3:
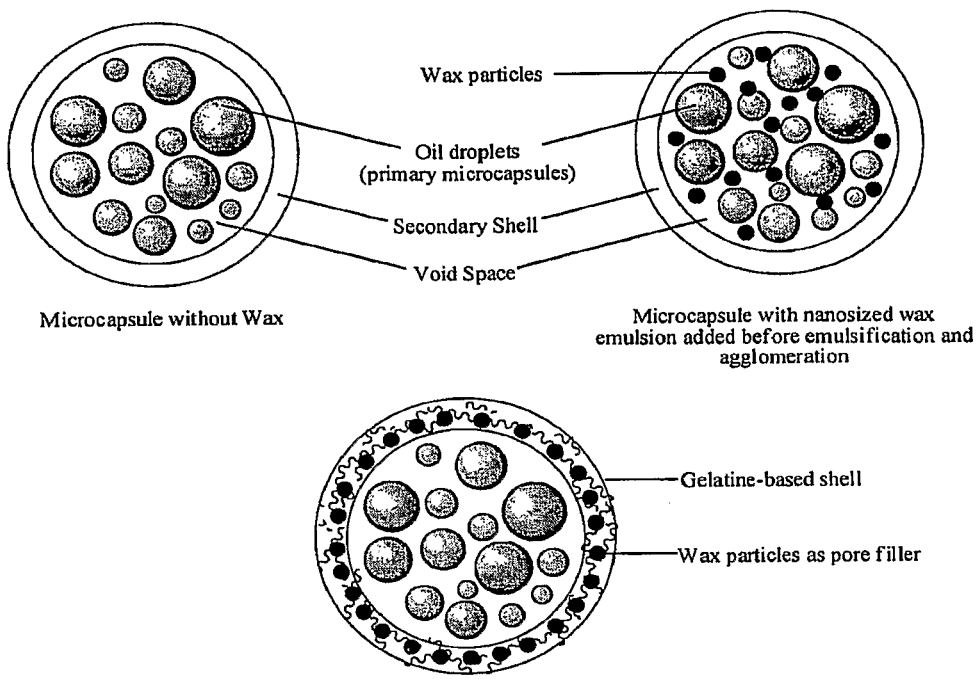
FIG. 3 is a group of three schematics of multicore microcapsules, one formed without the addition of wax, one formed by adding a wax emulsion before emulsification and agglomeration of the microcapsule, and one formed by adding wax particles after shell formation, where the wax particles block the pores of the secondary (outer) shell material.
Figure 4:
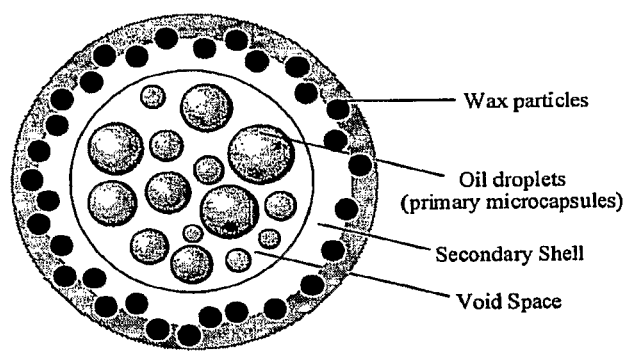
FIG. 4 is a schematic of a multicore microcapsule with wax particles added after shell formation (e.g., before spray drying).
Figure 5:
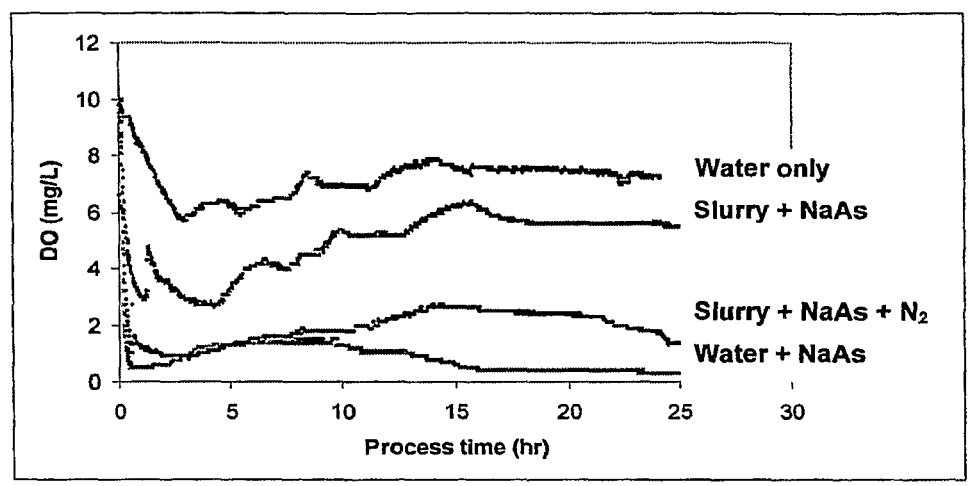
FIG. 5 is a graph of dissolved oxygen (mg/L) during preparation of a slurry with no Bloom fish gelatin.

Hydrophobic materials such as waxes can possess good moisture barrier properties, especially when compared to proteins and carbohydrates. Thus, disclosed herein are microcapsules where void volumes inside the multicore agglomeration contain wax particles. The addition of wax particles can fill the space in the agglomeration as well as the shell pores (FIG. 3). The wax can be added at various points along the microcapsule preparation process. For example, the wax (e.g., in a microemulsion of wax particles) can be added to the emulsion and/or aqueous mixture before coacervation. Alternatively or additionally, the wax can be added after shell formation and crosslinking (e.g., prior to spray drying). In this way, the wax can form a protective layer, therefore improving the moisture and oxygen barrier of the microcapsules (FIG. 4).

Co-Spray Drying Protective Saccharides and/or Proteins after Shell Formation and Crosslinking After the shell forms and is hardened by crosslinking, the microcapsules can be used directly in relevant applications in the form of a slurry or converted into a dry powder product by a dehydration process such as spray drying. Co-spray drying the disclosed microcapsules with protective materials can further improve stabilization of the loading substance. The protective compositions include, but are not limited to, lipids and waxes, carbohydrates, saccharides, amino acids, peptides, and proteins, as are described herein. By filling the pores of the shell and/or coating the shell surface, the protective materials can provide additional barriers to moistures and oxygen after co-spray drying. One or more of these protective compositions can be added to the slurry of microcapsule either in dry form or as a solution (e.g., dissolved in water). The protective compositions can be applied just before spray drying the slurry, allowing enough time to dissolve and to be mixed.

Carbohydrates have higher glass transition temperatures (i.e., more stable in terms of molecular mobility) than proteins and lipids. Carbohydrates are also better oxygen barrier than proteins and lipids (when in dry state). Co-spray drying microcapsules with carbohydrates can form a more stable matrix, which can provide better protection from oxygen attack at the encapsulated loading substances. Polysaccharides co-spray dried with the microcapsules can provide enhanced impermeability mainly by forming protective matrix as a coating layer on the surface of microcapsule shell.

When the coating materials bear amphiphilic moieties, such film-forming materials show improved properties of both moisture and oxygen barriers because of their hydrophobic moieties. Examples of this type of protective materials are disclosed herein and include gum arabic and modified starch, such as starch sodium octenyl succinate. Besides the matrix coating on the shell surface, medium sized carbohydrate molecules or small sugars also diffuse into the porous network of the shell polymers and block the path of oxygen and/or volatile compounds such as off-flavor and off-odor.

Incorporating proteins into the microcapsule slurry before spray drying can help produce bland and stable powder, with improved drying performance. Heat denatured proteins can undergo irreversible thermal gelation, which forms stable coating on the surface of the microcapsules. Heating the mixture before drying can also reduce off flavor compounds. The protein co-spray drying compositions can also include plasticizers such as glycerol, sorbitol, mono-, di- or oligosaccharides (e.g., lactose). Small molecules such as oligopeptides and hydrophobic amino acids can also fill in the porous molecular network of the shell materials, in addition to film-formation on the surface of microcapsules for coating.

Incorporating Drying/Anticaking Agents to Improve Powder Flowability

Drying agents or anticaking agents can also be used to help produce free flowing powders. Typically, drying agents have high porosity, which can help adsorb surface oil and flavor compounds due to the raw materials, or the oxidation of lipids. Examples of suitable drying and/or anticaking agents include, but are not limited to, HUBERSORB™ and ZEOTHIX™ (J.M. Huber Corp; Harve de Grace, Md.) and CAPSUL™ (from National Starch & Chemical Co.) and VITACEL™ (J. Rettenmair USA; Schoolcraft, Mich.).

Incorporating Antioxidants into the Powder

In other examples, the disclosed herein are methods for incorporating antioxidants into and/or onto the primary shell, the outer shell, or both primary and outer shell materials. The disclosed methods comprise providing a microcapsule, providing an emulsion comprising a polymer component and an antioxidant; combining the emulsion and the microcapsule, to thereby provide a microcapsule with a shell material comprising the antioxidant. Suitable antioxidants include, but are not limited to, $CoQ_{10}$, lutein, zeaxanthan, carotene, and combinations thereof. These can be used alone or in addition to the amino acids, proteins, saccharides, or waxes disclosed herein.

The microcapsule can be any microcapsule, but particularly suitable microcapsules are those disclosed herein. Such microcapsules can be prepared by, for example, providing an emulsion comprising a first polymer component, a loading substance, a second polymer component; adjusting pH, temperature, concentration, mixing speed, or a combination thereof to form an agglomeration of primary microcapsules, wherein each individual primary microcapsule has a primary shell, wherein the loading substance is encapsulated by the primary shell, wherein the agglomeration is encapsulated by an outer shell, and wherein the primary and outer shell comprise the first and second polymer components. The resulting agglomeration can then be combined with an emulsion of the antioxidant and a third polymer component, which can be the same as or different from either the first or second polymer components. The resulting suspension can then be cooled and the coated microcapsules can be dried. In many suitable examples, the microcapsules can be included in a slurry that contains the antioxidants and the slurry can be spray dried.

Incorporating Zinc into the Powder

In other examples, the disclosed herein are methods for incorporating zinc into and/or onto the primary shell, the outer shell, or both primary and outer shell materials. The disclosed methods comprise providing a microcapsule, providing an emulsion comprising a polymer component and zinc; combining the emulsion and the microcapsule, to thereby provide a microcapsule with a shell material comprising zinc. Zinc can be used alone or in addition to the amino acids, proteins, saccharides, or waxes disclosed herein.

The microcapsule can be any microcapsule, but particularly suitable microcapsules are those disclosed herein. Such microcapsules can be prepared by, for example, providing an emulsion comprising a first polymer component, a loading substance, a second polymer component; adjusting pH, temperature, concentration, mixing speed, or a combination thereof to form an agglomeration of primary microcapsules, wherein each individual primary microcapsule has a primary shell, wherein the loading substance is encapsulated by the primary shell, wherein the agglomeration is encapsulated by an outer shell, and wherein the primary and outer shell comprise the first and second polymer components. The resulting agglomeration can then be combined with an emulsion of the antioxidant and a third polymer component, which can be the same as or different from either the first or second polymer components. The resulting suspension can then be cooled and the coated microcapsules can be dried. In many suitable examples, the microcapsules can be included in a slurry that contains zinc and the slurry can be spray dried.

Specific Examples

In a specific example, disclosed herein are processes for preparing a microcapsule, comprising providing an emulsion comprising a first polymer component and a composition comprising a saccharide, a wax, or combination thereof; adding a loading substance, a second polymer component, and, optionally, the composition, to the emulsion; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; and further cooling the aqueous mixture to form an outer shell around the agglomeration, wherein the primary shell material, the outer shell, or both comprises the saccharide, the wax, or combination thereof.

In another specific example, disclosed herein are processes for preparing a microcapsule, comprising providing an emulsion comprising a first polymer component, a loading substance, and a second polymer component; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; adding an composition comprising a saccharide to the aqueous mixture; and further cooling the aqueous mixture to form an outer shell around the agglomeration, wherein the primary shell material, the outer shell, or both comprises the saccharide.

In yet another specific example, disclosed herein are processes for preparing a microcapsule, comprising providing a slurry of one or more microcapsules, wherein the microcapsule comprises a shell material and a loading substance; adding a composition comprising one or more amino acid, protein, saccharide, wax, an antioxidant, zinc, or combinations thereof to the slurry; and then drying the slurry.

In still another specific example, disclosed herein are processes for preparing a microcapsule, comprising providing an emulsion comprising a first polymer component, a loading substance, a second polymer component, and a chelator to the emulsion; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; and further cooling the aqueous mixture to form an outer shell around the agglomeration.

Formulation Vehicles

Also disclosed herein are formulation vehicles comprising the microcapsules disclosed herein. Any of the microcapsules described herein can be incorporated into a formulation vehicle. Examples of formulation vehicles are provided herein and include, but are not limited to, foodstuffs, beverages, nutraceutical formulations, pharmaceutical formulations, lotions, creams, or sprays. In some other specific examples, the disclosed emulsions and/or microcapsules can be incorporated into gels, gel capsules, or tablets. Other vehicles include powders or powders coated with a polymer. Such vehicles can be given orally or, in the case of powders for example, sprinkled onto food or beverages.

Supplements

Also, disclosed herein are nutritional supplements that comprise the microcapsules disclosed herein. A nutritional supplement is any compound or composition that can be administered to or taken by a subject to provide, supply, or increase a nutrient(s) (e.g., vitamin, mineral, essential trace element, amino acid, peptide, nucleic acid, oligonucleotide, lipid, cholesterol, steroid, carbohydrate, and the like). For example, a nutritional supplement can comprise a composition comprising one or more loading substances disclosed herein.

The nutritional supplement can comprise any amount of the microcapsules disclosed herein, but will typically contain an amount determined to supply a subject with a desired dose of a loading substance (e.g., EPA and/or DHA). The exact amount of microcapsules required in the nutritional supplement will vary from subject to subject, depending on the species, age, weight and general condition of the subject, the severity of any dietary deficiency being treated, the particular mode of administration, and the like. Thus, it is not possible to specify an exact amount for every nutritional supplement. However, an appropriate amount can be determined by one of ordinary skill in the art using only routine experimentation given the teachings herein.

The nutritional supplement can also comprise other nutrient(s) such as vitamins other trace elements, minerals, and the like. Further, the nutritional supplement can comprise other components such as preservatives, antimicrobials, anti-oxidants, chelating agents, thickeners, flavorings, diluents, emulsifiers, dispersing aids, or binders.

The nutritional supplements are generally taken orally and can be in any form suitable for oral administration. For example, a nutritional supplement can typically be in a tablet, gel-cap, capsule, liquid, sachets, or syrup form.

The nutritional supplements can be designed for humans or animals, based on the recommended dietary intake for a given individual. Such considerations are generally based on various factors such as species, age, and sex as described above, which are known or can be determined by one of skill in the art. In one example, the disclosed supplements can be used as a component of feed for animals such as, but not limited to, livestock (e.g., pigs, chickens, cows, goats, horses, and the like) and domestic pets (e.g., cats, dogs, birds, and the like).

Pharmaceutical Formulations

Also, pharmaceutical formulations comprising the disclosed microcapsules are disclosed herein. A suitable pharmaceutical formulation can comprise any of the disclosed compositions with a pharmaceutically acceptable carrier. For example, a pharmaceutical formulation can comprise one or more of the disclosed emulsions and/or microcapsules and a pharmaceutically acceptable carrier. The disclosed pharmaceutical formulations can be used therapeutically or prophylactically.

By "pharmaceutically acceptable" is meant a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy*, 21$^{st}$ ed., Lippincott Williams & Wilkins, Philadelphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8 (e.g., from about 7 to about 7.5). Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate.

Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like can be desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids, or binders can be desirable.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Foodstuffs

Also disclosed herein are foodstuffs that comprise any of the disclosed microcapsules. By "foodstuff" is meant any article that can be consumed (e.g., eaten, drank, or ingested) by a subject. In one example, the disclosed compositions can be used as nutritional supplements that are added to a foodstuff. For example, the disclosed microcapsules can be added to food or beverages. In this sense, the disclosed compositions can be prepared in, for example, a powdered form and contained in articles such as sachets or shakers, which can be used to pour or sprinkle the disclosed compositions onto and into food and beverages.

In some examples, the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or pet companion food. In other examples, the foodstuff is bread, tortillas, cereal, sausage, chicken, ice cream, yogurt, milk, salad dressing, rice bran, fruit juice, a dry beverage powder, liquid beverage, rolls, cookies, crackers, fruit pies, or cakes.

Emulsions

Also disclosed are compositions comprising a spray dried emulsion comprising a first polymer component and a loading substance, and a residue of one or more compositions comprising an amino acid, protein, saccharide, wax, or combination thereof. The first polymer component can be any of the first polymer components disclosed herein. Likewise, the loading substance can be any of the loading substances disclosed herein. Still further, the amino acid, protein, saccharide, wax, and combinations thereof can be any of those disclosed herein.

Methods of Use

The disclosed microcapsules also have a wide variety of uses. For example, disclosed herein are methods of delivering a loading substance to a subject by administering to the subject a microcapsule as disclosed herein. Also disclosed is the use a microcapsule as disclosed herein to prepare a medicament for delivering a loading substance to a subject.

The use of microcapsules can protect certain compositions from oxidation and degradation, keeping the loading substance fresh. Also, because microcapsules can hide the unpleasant odor or taste of certain compositions, the methods disclosed herein can be particularly useful for delivering and supplementing unpleasant compositions. Still further, the use of microcapsules can allow various loading substances to be added to food articles which are otherwise not amenable to supplementation. For example, omega-3 fatty acids can degrade or oxidize in air and can be sensitive to food preparation techniques (e.g., baking). By the use of microencapsulated omega-3 fatty acids, these compositions can be added to food without significant degradation during food preparation.

Particularly suitable microcapsules include those that are resistant to rupture during the preparation of the food article (including packaging, transportation, and storage of the food article). In some examples, the microcapsules can be of a size and consistency that does not detract from the texture and constitution of the food article.

In a particular example, the disclosed microcapsules (including nutritional supplements, pharmaceutical formulations, delivery devices, and foodstuffs that contain the disclosed microcapsules) can be used as a source of fatty acids (e.g., omega-3 fatty acids), lowering triglycerides and influencing diabetes related biochemistry. In another particular example, disclosed herein are methods of supplementing omega-3 fatty acids in a subject by administering an effective amount of a microcapsule disclosed herein, wherein the loading substance comprises an omega-3 fatty acid. In another example, disclosed herein are methods of lowering cholesterol levels, triglyceride levels, or a combination thereof in a subject by administering an effective amount of an emulsion and/or microcapsule disclosed herein.

Omega-3 fatty acids are vital to everyday life and function. For example, the beneficial effects of omega-3 fatty acids like cis-5,8,11,14,17-eicosapentaenoic acid (EPA) and cis-4,7,10, 13,16,19-docosahexaenoic acid (DHA) on lowering serum triglycerides are well established. These compounds are also known for other cardioprotective benefits such as preventing cardiac arrhythmias, stabilizing atherosclerotic plaques, reducing platelet aggregation, and reducing blood pressure. See e.g., Dyrberg et al., In: Omega-3 Fatty Acids: Prevention and Treatment of Vascular Disease. Kristensen et al., eds., Bi & Gi Publ., Verona-Springer-Verlag, London, pp. 217-26, 1995; O'Keefe and Harris, *Am. J. Cardiology* 2000, 85:1239-41; Radack et al., "The effects of low doses of omega-3 fatty acid supplementation on blood pressure in hypertensive subjects: a randomized controlled trial." *Arch. Intern. Med.* 1991, 151:1173-80; Harris, "Extending the cardiovascular benefits of omega-3 fatty acids." *Curr Atheroscler Rep* 2005, 7:375-80; Holub, "Clinical nutrition: 4 omega-3 fatty acids in cardiovascular care." *CMAJ* 2002, 166(5):608-15. Indeed, the American Heart Association has also reported that omega-3 fatty acids can reduce cardiovascular and heart disease risk. Other benefits of omega-3 fatty acids are those related to the prevention and/or treatment of inflammation and neurodegenerative diseases, and to improved cognitive development. See e.g., Sugano and Michihiro, "Balanced intake of polyunsaturated fatty acids for health benefits." *J. Oleo Sci.* 2001, 50 (5):305-11.

The fatty acids EPA and DHA can be synthesized in the human body from α-linolenic acid (18:3); however, the conversion rate from this precursor molecule is limited (Muskiet et al., "Is docosahexaenoic acid (DHA) essential? Lessons from DHA status regulation, our ancient diet, epidemiology and randomized controlled trials." *J. Nutr.* 2004, 134(1):183-6). Accordingly, EPA and DHA in the body are primarily derived from dietary sources (e.g., oily fish). Diets rich in fish oils are known to have many beneficial effects for heart disease, cancer, arthritis, allergies, and other chronic diseases. Epidemiological clinical trials have shown that increasing the dietary intake of omega-3 fatty acids, in the form of fish or of fish oil supplements, may reduce various risk factors associated with cardiovascular disease. See e.g., The American Heart Association, Scientific Statement, "Fish Consumption, Fish Oil, Omega-3 Fatty Acids and Cardiovascular Disease," November 2002; Appel et al., "Does supplementation of diet with 'fish oil' reduce blood pressure? A meta-analysis of controlled clinical trials." *Arch. Intern. Med.* 1993, 153(12): 1429-1438; GISSI-Prevenzione Investigators. "Dietary supplementation with omega-3 polyunsaturated fatty acids and vitamin E after myocardial infarction: results of the GISSI-Prevenzione trial." *Lancet* 1999, 354:447-55.

Despite the strong evidence for the benefit of omega-3 fatty acids like EPA and DHA in prevention of cardiovascular disease, the average daily consumption of these fatty acids by North Americans is estimated to be between 0.1 to 0.2 grams, compared to a suggested daily intake of 0.65 grams to confer benefit (Webb, "Alternative sources of omega-3 fatty acids." *Natural Foods Merchandiser* 2005, XXVI(8):40-4). Since altering dietary patterns of populations is difficult and many people do not like to eat fish, dietary supplementation with EPA and DHA is an important approach to addressing this problem. Unfortunately, many supplements of omega-3 fatty acids are sensitive to oxidation and can be foul smelling and tasting. Further, compliance with dietary supplement regimens requires discipline, which is often wanting. In light of the health benefits of omega-3 fatty acids, the disclosed microcapsules can be used to deliver omega-3 fatty acids to a subject.

In the disclosed methods of use, the emulsions and/or microcapsules that are administered can be any of the compositions disclosed herein. For example, the disclosed microcapsules can be used in the disclosed methods in the form of any of the nutritional supplements disclosed herein. In another example, the disclosed microcapsules can be used in the disclosed methods in the form of any of the pharmaceutical formulations disclosed herein. In still another example, the disclosed microcapsules can be incorporated in any of the delivery devices disclosed herein, or incorporated into any foodstuff disclosed herein and used in the disclosed methods.

It is contemplated that the methods disclosed herein can be accomplished by administering various forms of the disclosed microcapsules. For example, one can administer any of the pharmaceutical formulations with any of the foodstuffs disclosed herein. In another example, one can administer a tablet or capsule with any of the nutritional supplements disclosed herein. In yet another example, one can administer any of the pharmaceutical formulations with any of the delivery devices and nutritional supplement disclosed herein, and the like.

Dosage

When used in the above described methods or other treatments, or in the nutritional supplements, pharmaceutical formulations, delivery devices, or foodstuffs disclosed herein, an "effective amount" of one of the disclosed microcapsules can be employed in pure form or, where such forms exist, in pharmaceutically acceptable salt form, and with or without a pharmaceutically acceptable excipient, carrier, or other additive.

The specific effective dose level for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of a composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose.

The dosage can be adjusted by the individual physician or the subject in the event of any counterindications. Dosage can vary, and can be administered in one or more dose administrations daily, for one or several days. Guidance can be found in the literature for appropriate dosages for given classes of pharmaceutical products.

Further, disclosed are methods for delivering a disclosed composition to a subject by administering to the subject any of the nutritional supplements, pharmaceutical formulations, delivery devices, and/or foodstuffs disclosed herein. The disclosed compositions (including nutritional supplements, delivery devices, and pharmaceutical formulations) can typically be administered orally.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Ocean Nutrition Canada, Ltd. (Dartmouth, Canada), Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17

(John Wiley and Sons, 1991); Rodd's Chemistry of Carbon Compounds, Volumes 1-5 and Supplements (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Control Example A

Preparing Omega-3 Microcapsules Using 275 Bloom Gelatin

A 275 Bloom porkskin gelatin (44 g) was dissolved in water (482 g) and the solution was heated to 50° C. The initial pH of the gelatin solution was 4.638. Sodium ascorbate (7.3 g) was then added to the gelatin solution and the pH was 5.271.

High DHA fish oil (72.0 g; XODHA from Ocean Nutrition Canada Ltd.) was added to the gelatin solution and emulsified using a POLYTRON™ homogenizer at 7,500 rpm for 4 minutes. The emulsion was examined under a microscope after emulsification to verify that the oil droplets were small and uniform (about 1-5 µm in diameter).

To a 2 L reactor, distilled water (890 g) was added and the temperature was maintained at 50° C. The emulsion was then added to the distilled water in the reactor and the pH was found to be 5.058. Sodium polyphosphate (4.4 g) dissolved in distilled water (84 g) was added to the diluted emulsion in the reactor and the resulting mixture had a pH of 5.821.

pH was then lowered with 10% phosphoric acid in order to form agglomerations of the primary microcapsules. When pH was further lowered to 4.686, secondary microcapsules formed 30-50 µm agglomerations. The mixture was cooled at an average cooling rate of 1° C./5 minutes from 50° C. to 4° C.

After pH was adjusted to 6.0 by adding 10% NaOH, a 1% w/w transglutaminase preparation (Ajinomoto USA Inc., Fort Lee, N.J.) was added and the temperature was maintained at room temperature (~25° C.) for 16 hours.

The slurry was then ready for food applications. It was also spray dried to produce a free flowing powder. This powder had an induction period of 44.7 hours determined at 65° C. under an initial pressure of approximately 550 kPa of oxygen by using an Oxipres (Mikrolab Aarhus A/S, Hojbjerg, DNK).

Control Example B

Preparing Omega-3 Microcapsules Using 240 Bloom Gelatin

A 240 Bloom fish gelatin (44 g) was dissolved in water (320 g) and the solution was heated to 40° C. The initial pH of the gelatin solution was 5.807. Sodium ascorbate (7.3 g) was then added to the gelatin solution and the pH was 5.902.

High DHA fish oil (72.0 g; XODHA from Ocean Nutrition Canada Ltd.) was added to the gelatin solution and emulsified using, a POLYTRON™ homogenizer at 7,500 rpm for 4 minutes. The emulsion was examined under a microscope after emulsification to verify that the oil droplets were small and uniform (about 1-5 µm in diameter).

To a 2 L reactor, distilled water (1051 g) was added and the temperature was maintained at 40° C. The emulsion was then added to the distilled water in the reactor and the pH was found to be 5.812. Sodium polyphosphate (4.4 g) dissolved in distilled water (84 g) was then added to the diluted emulsion in the reactor and the resulting mixture had a pH of 6.512.

pH was then lowered with 10% phosphoric acid in order to form agglomerations of the primary microcapsules. When pH was further lowered to 4.773, secondary microcapsules formed 30-50 µm agglomerations. The mixture was cooled at an average cooling rate of 1° C./5 minutes from 40° C. to 5° C.

After pH was adjusted to 6.0 by adding 10% NaOH, a 1% w/w transglutaminase preparation (Ajinomoto USA Inc., Fort Lee, N.J.) was added for crosslinking and hardening the shell of the microcapsules at 5° C. for 1 hour, 15° C. for 8 hour, and 20° C. for 9 hours.

The slurry was then ready for food applications. It was also spray dried to produce a free flowing powder. This powder had an induction period of 43.5 hours determined at 65° C. under an initial pressure of approximately 550 kPa of oxygen by using an Oxipres (Mikrolab Aarhus A/S, Hojbjerg, DNK).

Control Example C

Preparing Omega-3 Microcapsules Using 0 Bloom Gelatin

A 0 Bloom fish gelatin (44 g; Kenny & Ross Ltd., Shelburne, NS) was dissolved in water (323 g) and the solution was heated to 35.6° C. The initial pH of the gelatin solution was 5.807. Sodium ascorbate (7.3 g) was then added to the gelatin solution and the pH was 6.042. Sodium polyphosphate (4.4 g) dissolved in distilled water (84 g) was then added to the gelatin solution. The mixture had a pH of 6.306 at 34.1° C., which was adjusted to 4.9 with 10% phosphoric acid.

High DHA fish oil (72.6 g; XODHA from Ocean Nutrition Canada Ltd.) was mixed with the gelatin solution and emulsified using a POLYTRON™ homogenizer at 7,500 rpm for 4 minutes. The emulsion was examined under a microscope after emulsification to verify that the oil droplets were small and uniform (about 1-5 µm in diameter).

To a 2 L reactor, distilled water (1060 g) was added and the temperature was maintained at 35° C. The emulsion was then added to the distilled water in the reactor and the pH was found to be 4.9412. While the mixture was agitated, pH was lowered with 10% phosphoric acid in order to form agglomerations of primary microcapsules. After pH was lowered to 4.751, the secondary microcapsules were around 40 µm in diameter. The mixture was cooled at an average cooling rate of 1° C./5 minutes from 35° C. to 5° C.

After pH was adjusted to 6.0 by adding 10% NaOH, a 1% w/w transglutaminase preparation (Ajinomoto USA Inc., Fort Lee, N.J.) was added for crosslinking the shell of the microcapsules at 5° C. for 5 hours, followed by enzymatic hardening at 20° C. for 10 hours.

The finished suspension of microcapsules was then ready for food applications. It was also spray dried to produce a free flowing powder. This powder had an induction period of 36.9 hours determined at 65° C. under an initial pressure of approximately 550 kPa of oxygen by using an Oxipres (Mikrolab Aarhus A/S, Hojbjerg, DNK).

Examples 1

Preparing Omega-3 Microcapsule by Incorporating Chitosan Before Coacervation

Example 1.1

Preparing Omega-3 Microcapsules with 240 Bloom Fish Gelatin and Chitosan (Added Before Emulsification and Coacervation)

A 240 Bloom fish gelatin (44 g; from Lapi Gelatine S.p.A., Empoli, Italy) was dissolved in water (256 g) with sodium ascorbate (7.3 g) and heated to 41° C. A 1% chitosan solution in 1% acetic acid (44 g) was added to the gelatin solution, taking into account the amount of additional water to make the total mass of water 320 g. Phosphoric acid (10% solution, 17.6 mL) was added to the gelatin solution to reach a pH of about 4.5. High DHA fish oil (72.0 g; XODHA from Ocean Nutrition Canada Ltd.) was then added to the gelatin-chitosan solution and emulsified using a POLYTRON™ homogenizer at 7,500 rpm for 4 minutes.

To a 2 L reactor, distilled water (752 g) was added and the temperature was maintained at 41° C. The emulsion was then added to the distilled water in the reactor and the mixture was stirred at 41° C. Sodium polyphosphate (4.4 g) dissolved in distilled water (300 g) was added in 50 mL aliquots to the diluted emulsion in the reactor. (The ratio of sodium polyphosphate to chitosan can range from 50:1 to 5:1; however, this particular example used a 10:1 ratio.) The mixture in the reactor had a pH of about 4.7 after all of the sodium polyphosphate solution was added.

While the mixture was agitated, pH was adjusted to 4.301 with 10% phosphoric acid to form 30-70 μm agglomerations of the primary microcapsules. The mixture was then cooled at an average cooling rate of 1° C./5 minutes from 41° C. to 3° C.

After pH was adjusted to 6.0 by adding 10% NaOH, a 1% w/w transglutaminase preparation (Ajinomoto USA Inc., Fort Lee, N.J.) was added. The slurry was then held at 3° C. for 1 hour for crosslinking, followed by enzymatic hardening at 15° C. for 8 hours and 20° C. for 10 hours.

The finished suspension of microcapsules was then ready for food applications. It was also spray dried to produce a free flowing powder. This powder had an induction period of 61 hours determined at 65° C. under an initial pressure of approximately 550 kPa of oxygen by using an Oxipres (Mikrolab Aarhus A/S, Hojbjerg, DNK). The induction period was improved with 17.4 hours better than the Control B sample.

Example 1.2

Preparing Omega-3 Microcapsules with 240 Bloom Fish Gelatin and Chitosan (by Using a Two-Step Method)

A 240 Bloom fish gelatin (44 g; from Lapi Gelatine S.p.A., Empoli, Italy) was dissolved in water (289 g) with sodium ascorbate (7.3 g) and heated to 41° C. Phosphoric acid (10% solution) was added to the gelatin solution to make a pH of about 4.5. A 1% chitosan solution in 1% acetic acid (31.4 g) was then added to the gelatin solution. High DHA fish oil (72.0 g; XODHA from Ocean Nutrition Canada Ltd.) was next added to the gelatin-chitosan solution and emulsified using a POLYTRON™ homogenizer at 7,500 rpm for 4 minutes.

To a 2 L reactor, distilled water (752 g) and sodium polyphosphate (3.14 g) were added and the temperature was maintained at 41° C. The emulsion was then added to the distilled water in the reactor and the mixture was stirred at 41° C.

Sodium polyphosphate (1.26 g) dissolved in distilled water (192 g) was added to a 1% acetic acid solution (192 g) containing 0.13 g of chitosan and stirred. (The ratio of sodium polyphosphate to chitosan in this particular example was 10:1.) This chitosan-polyphosphate mixture was then added to the diluted emulsion in the reactor to make agglomerated particles. The mixture was then cooled at an average cooling rate of 1° C./5 minutes from 41° C. to 3° C.

After pH was adjusted to 6.0 by adding 10% NaOH, a 1% w/w transglutaminase preparation (Ajinomoto USA Inc., Fort Lee, N.J.) was added. The slurry was then held at 3° C. for 1 hour for crosslinking, followed by enzymatic hardening at 15° C. for 8 hours and 20° C. for 10 hours.

The finished suspension of microcapsules was then ready for food applications. It was also spray dried to produce a free flowing powder. This powder had an induction period of 49.7 hours determined at 65° C. under an initial pressure of approximately 550 kPa of oxygen by using an Oxipres (Mikrolab Aarhus A/S, Hojbjerg, DNK). The induction period was 6.2 hours longer than the sample of Control B.

Examples 2

Preparing Omega-3 Microcapsules by Incorporating Chitosan, Lysine, and/or Glutamine after Coacervation and Shell Formation Example 2.1

Preparing Omega-3 Microcapsules Using 240 Bloom Fish Gelatin and Adding Chitosan after Agglomeration but Before Shell Formation A 240 Bloom fish gelatin (44 g; from Lapi Gelatine S.p.A., Empoli, Italy) was dissolved in water (320 g) and heated to 40° C. Sodium ascorbate (7.3 g) was also added to the gelatin solution. High DHA fish oil (72.0 g; XODHA from Ocean Nutrition Canada Ltd.) was then added to the gelatin solution and emulsified using a POLYTRON™ homogenizer at 7,500 rpm for 4 minutes.

To a 2 L reactor, distilled water (944 g) and sodium polyphosphate (4.4 g) were added and the temperature was maintained at 40° C. The emulsion was then added to the reactor. While the mixture was agitated, pH was adjusted to about 4.3 with 10% phosphoric acid to form about 30-60 μm agglomerations of the primary microcapsules.

The mixture was then cooled at an average cooling rate of 1° C./5 minutes from 40° C. to 3° C. When the temperature reached 23° C., chitosan (192 g of a 1% acetic acid solution containing 0.44 g chitosan) was added to the reactor. Cooling continued without interruption.

After pH was adjusted to 6.0 by adding 10% NaOH, a 1% w/w transglutaminase preparation (Ajinomoto USA Inc., Fort Lee, N.J.) was added. The slurry was then held at 3° C. for 1 hour for crosslinking, followed by enzymatic hardening at 15° C. for 8 hours and 20° C. for 10 hours.

The finished suspension of microcapsules was then ready for food applications. It was also spray dried to produce a free flowing powder. This powder had an induction period of 49.7 hours determined at 65° C. under an initial pressure of approximately 550 kPa of oxygen by using an Oxipres (Mikrolab Aarhus A/S, Hojbjerg, DNK). This induction period was 6.2 hours longer than the sample of its Control B.

Example 2.2

Preparing Omega-3 Microcapsules Using 0 Bloom Fish Gelatin Incorporated with Chitosan, Lysine, and Glutamine A 0 Bloom fish gelatin (88 g; Kenny & Ross Ltd., Shelburne, NS) was dissolved in water (640 g) and the solution was heated to 35° C. Sodium ascorbate (14.6 g) was also added to the gelatin solution. High DHA fish oil (144.0 g; XODHA from Ocean Nutrition Canada Ltd.) was mixed with the gelatin solution and emulsified using a POLYTRON™ homogenizer at 7,500 rpm for 4 minutes. The emulsion was examined under a microscope after emulsification to verify that the oil droplets were small and uniform (about 1-5 μm in diameter).

To a 3 L reactor, distilled water (2000 g) was added and the temperature was maintained at 35° C. The emulsion was then added to the distilled water in the reactor and the pH was found to be 5.98. Sodium polyphosphate (6.0 g) dissolved in distilled water (160 g) was next added to the diluted emulsion in the reactor. The resulting mixture in the reactor had a pH of 6.50.

While the mixture was agitated, pH was adjusted to 4.78 with 10% phosphoric acid in order to form agglomerations of primary microcapsules about 50 μm in diameter. The mixture was then cooled from 35° C. to 4° C. at an average cooling rate of 1° C./5 minutes.

After pH was adjusted to 6.0 by adding 10% NaOH, a 1% w/w transglutaminase preparation (Ajinomoto USA Inc., Fort Lee, N.J.) was added. The slurry was then held at 4° C. for 5 hours and then 8° C. for 6 hours for crosslinking. Next, the solution was warmed up to 20° C.

Two identical batches of this base slurry were prepared and mixed together for further treatment.

Example 2.2.1

Control

The base slurry from Example 2.2 (1000 g) was further crosslinked at room temperature (~25° C.) for 6 hours. This control slurry was then spray dried.

Example 2.2.2

Treatment with High MW Chitosan

The base slurry from Example 2.2 (1000 g) was treated with high MW chitosan (131.3 kDa) by first transferring the slurry into a 1.5 L reactor. A solution (250 g) of 1.0% w/w chitosan in 1.0% w/w acetic acid was prepared and diluted to 0.5% w/w with distilled water. This 0.5% chitosan solution was then slowly added to the base slurry in the 1.5 L reactor. The pH was adjusted to 6.0 and the mixture was stirred at room temperature (~25° C.) for 5 hours.

Example 2.2.3

Treatment with Low MW Chitosan

The base slurry from Example 2.2 (1000 g) was treated with low MW chitosan (5.3 kDa) slurry by first transferring the slurry into a 1.5 L reactor. A solution (200 g) of 1.0% w/w chitosan in 1.0% w/w acetic acid was prepared and diluted to 0.4% w/w with distilled water. This 0.4% chitosan solution was then slowly added to the slurry in the 1.5 L reactor. The pH was adjusted to 5.6 and the mixture was stirred at room temperature (~25° C.) for 5 hours.

Example 2.2.4

Treatment with Lysine and Glutamine

The base slurry from Example 2.2 (1000 g) was treated with lysine and glutamine by first transferring the slurry into a 1.5 L reactor. Lysine (5.0 g) in distilled water (40 g) was slowly added to the slurry in the 1.5 L reactor. The pH was adjusted to 6.0. After 2 hours, glutamine (2.0 g) in distilled water (60.0 g) was also slowly added to the slurry. The mixture was stirred at room temperature (~25° C.) for 3 hours.

Example 2.2.5

Treatment with High MW Chitosan and Glutamine

The base slurry from Example 2.2 (1000 g) was treated with high MW chitosan and glutamine by first transferring the slurry into a 1.5 L reactor. A solution (250 g) of 1.0% w/w chitosan in 1.0% w/w acetic acid was prepared and diluted to 0.5% w/w with distilled water. This 0.5% chitosan solution was then slowly added to the slurry in the 1.5 L reactor. The pH was adjusted to 6.0. After 2 hours, glutamine (2.0 g) in distilled water (60.0 g) was also slowly added to the slurry. The mixture was stirred at room temperature (~25° C.) for 3 hours.

The finished slurry samples of microcapsules from Examples 2.2.1 through 2.2.5 were then spray dried to produce free flowing powder products. These sample powders all had improved induction period as compared to the control sample 2.2.1 and Control Sample C (Table 1).

TABLE 4

Results of chitosan, lysine, and glutamine treatment

| Example # | Free oil (%) | Induction period (hr) |
| --- | --- | --- |
| 2.2.1 | 0.032 | 44.4 |
| 2.2.2 | 0.027 | 55.9 |
| 2.2.3 | 0.081 | 68.0 |
| 2.2.4 | 0.035 | 80.2 |
| 2.2.5 | 0.016 | 83.0 |

Example 3

Preparing Omega-3 Microcapsules Using 0 Bloom Gelatin with Wax Incorporation Before Agglomeration and Shell Formation A 0 Bloom fish gelatin (44.1 g) was dissolved in water (323.8 g) and heated to 35° C. Sodium ascorbate (7.32 g) and a microemulsion of carnauba wax (7.90 g; ME28230 from Michelman Inc., Cincinnati, Ohio) were added to the gelatin solution. High DHA fish oil (73.54 g; XODHA from Ocean Nutrition Canada Ltd.) was added to the gelatin solution and emulsified using a POLYTRON™ homogenizer at 7,500 rpm for 4 minutes.

The emulsion was transferred to a 2 L reactor containing distilled water (1061.4 g) maintained at 35° C. The emulsion had a pH of 5.88 at 35° C. A 5% sodium polyphosphate solution (88.0 g) was added to the mixture and the pH was found to be 6.59 at 35° C. While the mixture was agitated, pH was adjusted to 4.68 at 35° C. with 10% phosphoric acid to form 30-60 μm agglomerations of the primary microcapsules.

The resulting mixture of multicore microcapsules was then cooled at an average cooling rate of 1° C./5 minutes from 35° C. to 4° C. After pH was adjusted to 6.0 by adding 10% NaOH, a 1% w/w transglutaminase preparation (Ajinomoto USA Inc., Fort Lee, N.J.) was added. The slurry was then held at 5° C. for 5 hours for crosslinking, followed by enzymatic hardening at 20° C. for 10 hours.

The finished suspension of microcapsules was then ready for food applications. It was also spray dried to produce a free flowing powder. This powder had an induction period of 70.5 hours compared to 36.9 hours for a control without wax incorporation (e.g., Control Example C).

Example 4

Preparing Omega-3 Microcapsules Using 275 Bloom Gelatin with Wax Incorporation after Shell Formation A 275 Bloom fish gelatin (40.92 g) was dissolved in water (452 g) and heated to 50° C. Sodium ascorbate (6.82 g) was added to the gelatin solution. High DHA fish oil (68.25 g; XODHA from Ocean Nutrition Canada Ltd.) was added to the gelatin solution and emulsified using a POLYTRON™ homogenizer at 6,400 rpm for 11 minutes.

The emulsion was transferred to a 2 L reactor containing distilled water (833.3 g) maintained at 50° C. The emulsion had a pH of 5.23 at 51.8° C. A 5% sodium polyphosphate solution (82.5 g) was added to the mixture and the pH was found to be 5.66 at 50.4° C. While the mixture was agitated, pH was adjusted to 4.80 at 50.4° C. with 10% phosphoric acid to form about 30-60 μm agglomerations of the primary microcapsules.

The mixture of multicore microcapsules was then cooled at an average cooling rate of 1° C./5 minutes from 50° C. to 4° C. After pH was adjusted to 6.0 by adding 10% NaOH, a 1% w/w transglutaminase preparation (Ajinomoto USA Inc., Fort Lee, N.J.) was added. The slurry was then held at room temperature (~25° C.) for 16 hours for crosslinking and hardening.

The pH was adjusted to 9.3 and a microemulsion of carnauba wax (187 g; ME62125Am, Michelman Inc.) was added. The mixture had a pH of 8.69 and contained 46.7 g total weight of carnauba wax.

The finished suspension of microcapsules was then ready for food applications. It was also spray dried to produce a free flowing powder. This powder had an induction period of 80.0 hours compared to 44.7 hours for a control without wax incorporation (e.g., Control Example A).

Examples 5

Preparing Omega-3 Microcapsules Using 240 Bloom Gelatin with Incorporated Carbohydrates and Proteins after Shell Formation Example 5.1

Preparing Base Slurry of Fish Oil Microcapsule Using 240 Bloom Fish Gelatin

A 240 Bloom fish gelatin (325.8 g) was dissolved in water (3599 g) in a 10,000 g reactor and heated to 40° C. under agitation. Sodium ascorbate (49.4 g) and a 20% phosphoric acid solution (60 mL) were added to the gelatin solution. High DHA fish oil (565 g; XODHA from Ocean Nutrition Canada Ltd.) was added to the gelatin solution and emulsified using a high shear pump until the droplets were 1-5 μm in diameter. Distilled water (5453.4 g) was added to the reactor and the temperature was maintained at 40° C.

Sodium polyphosphate (32.6 g) dissolved in distilled water (100 g) was then added to the diluted emulsion in the reactor. The pH was adjusted to 4.57 with 20% phosphoric acid (about 100 mL) to form about 30 μm agglomerations of the primary microcapsules.

The mixture was then cooled from 40° C. to 6° C. at an average cooling rate of 1° C./5 minutes. After pH was adjusted to 6.0 by adding 10% NaOH, a 1% w/w transglutaminase preparation (Ajinomoto USA Inc., Fort Lee, N.J.) was added. The slurry was then crosslinked at 15° C. for 9 hours and 20° C. for 8 hours.

The finished suspension of microcapsules was then ready for coating processes. The suspension could also be spray dried to produce a free flowing powder.

Example 5.2

Incorporating Modified Starch in the Microcapsules

Modified starch (40 g; N-LOK from National Starch & Chemical Co., Bridgewater, N.J.) was dissolved in water (60 g) under agitation. The base slurry prepared in Example 5.1 (600 g) was transferred into a 1000 mL beaker and the slurry was stirred with a magnet bar on a hot plate. The modified starch solution was then added to the slurry and stirring was continued for 30 minutes. The slurry was spray dried to produce a free flowing powder.

Example 5.3

Incorporating Modified Starch and Lactose in the Microcapsules

Modified starch (20 g; N-LOK from National Starch & Chemical Co., Bridgewater, N.J.) was dissolved in water (30 g) under agitation to make a 40% suspension. Lactose (25 g) was dissolved in water (25 g) under agitation to make a 50% solution. The base slurry prepared in Example 5.1 (600 g) was transferred into a 1000 mL beaker and the slurry was stirred with a magnet bar on a hot plate. The starch and lactose solutions were mixed thoroughly and added to the base slurry, which was stirred for 30 minutes. The slurry was spray dried to produce a free flowing powder.

Example 5.4

Incorporating Lactose in Microcapsules

Lactose (50 g) was dissolved in water (50 g) by heating and agitation. Tween 80 (5 g) was then added to the lactose solution. The base slurry prepared in Example 5.1 (600 g) was transferred into a 1000 mL beaker and the slurry was stirred with a magnet bar on a hot plate. The lactose-Tween 80 solution was added to the slurry and stirring was continued for 30 minutes. The slurry was spray dried to produce a free flowing powder.

Example 5.5

Incorporating Maple Syrup in Microcapsules

The base slurry prepared in Example 5.1 (600 g) was transferred into a 1000 mL beaker and the slurry was stirred with a magnet bar on a hot plate. Maple syrup (100 g; from a supermarket) was added in the slurry and stirring was continued for 30 minutes. The slurry was spray dried to produce a free flowing powder.

Example 5.6

Incorporating Sucrose in Microcapsules

Sucrose (50 g) was dissolved in water (50 g) by heating and agitation. Tween 80 (5 g) was then added to the sucrose solution. The base slurry prepared in Example 5.1 (600 g) was transferred into a 1000 mL beaker and the slurry was stirred with a magnet bar on a hot plate. The sucrose-Tween 80 solution was added to the slurry and stirring was continued for 30 minutes. The slurry was spray dried to produce a free flowing powder.

Example 5.7

Incorporating Methylcellulose in Microcapsules

Hydroxypropylmethylcellulose (HPMC) (5 g; Methocel E3, from DOW Chemical Co., Midland, Mich.) was suspended in water (95 g) by heating and agitation. The base slurry prepared in Example 5.1 (600 g) was transferred into a 1000 mL beaker and the slurry was stirred with a magnet bar on a hot plate. The HPMC solution was added to the slurry and stirring was continued for 30 minutes. The slurry was spray dried to produce a free flowing powder.

Example 5.8

Incorporating Milk Protein in Microcapsules

A high calcium milk protein (50 g; Alaco 9090 from NZMP (North America) Inc., Santa Rosa, Calif.) was suspended in water (50 g) by heating and agitation. The base slurry prepared in Example 5.1 (600 g) was transferred into a 1000 mL beaker and the slurry was stirred with a magnet bar on a hot plate. The milk protein solution was then added to the slurry and stirring was continued for 30 minutes. The slurry was spray dried to produce a free flowing powder.

Example 5.9

Incorporating Whey Protein and Glycerin in Microcapsules

Whey protein (50 g; Alacen 841 from NZMP (North America) Inc., Santa Rosa, Calif.) was dissolved in water (50 g) by heating and agitation. Glycerin (5 g) was also added. The base slurry prepared in Example 5.1 (600 g) was transferred into a 1000 mL beaker and the slurry was stirred with a magnet bar on a hot plate. The whey protein-glycerin solution was added to the slurry and stirring was continued for 30 minutes. The slurry was spray dried to produce a free flowing powder.

TABLE 5

Effect of various carbohydrates and proteins on the stability of fish oil microcapsules

| Example # | Induction period (hr) |
| --- | --- |
| 5.1 | 36.0 |
| 5.2 | 91.0 |
| 5.3 | 91.0 |
| 5.4 | 116.0 |
| 5.5 | 116.0 |
| 5.6 | >116 |
| 5.7 | 36 |
| 5.8 | 63.0 |
| 5.9 | 62.0 |

Example 6

Preparing Omega-3 Microcapsules Using 0 Bloom Fish Gelatin with Improved Sensory by Nitrogen Purge An amount of 720 g of 0 Bloom fish gelatin solution (12% w/w, 35° C.) was prepared. Sodium ascorbate (3.6 g) was then added to the gelatin solution. High DHA fish oil (140 g; XODHA from Ocean Nutrition Canada Ltd.) was also added and the solution was emulsified using a POLYTRON™ homogenizer at 7,500 rpm for 4 minutes and under nitrogen purge.

Distilled water (1050 g) was added to each of two 2-L reactors and the temperature was maintained at 35° C. Sodium ascorbate (5.7 g) was also added to the water in each reactor. Half of the emulsion was transferred into each reactor (about 430 g). One reactor was used as a control (Example 6.1, under atmosphere), while the other reactor (Example 6.2) was under constant nitrogen purge in order to exclude oxygen from air and minimize the oxidative deterioration of the fish oil. The mixture in each reactor was under constant agitation and had a temperature of 36.0° C. and pH of 6.086.

A 5% sodium polyphosphate solution (89.4 g) was added to each reactor and the pH increased to 6.607. After pH was adjusted to 4.888 with 5% phosphoric acid, secondary microcapsules formed and the agglomerations had a diameter of about 50 μm in each reactor. The samples were then cooled from 35° C. to 5° C. at an average rate of 1° C./5 minutes.

After pH was adjusted to 6.0 with by adding 10% NaOH, a 1% w/w transglutaminase preparation (Ajinomoto USA Inc., Fort Lee, N.J.) was added. The slurry was then held at 5° C. for 5 hours for crosslinking, followed by enzymatic hardening at 20° C. for 10 hours.

The finished suspension of microcapsules was spray dried to produce a free flowing powder. The powder samples had an induction period of 50.8 and 50.3 hours, respectively. It was found, as shown in Table 3, that the nitrogen purge helped improve the sensory of the final product.

TABLE 6

Effect of exposing the slurry to air or nitrogen on sensory of fish oil microcapsules.

| Example # | Treatment | Odor | Flavor | IP (hr) |
| --- | --- | --- | --- | --- |
| 6.1 | No $N_2$ | Very sour, fishy | Sour dairy, slight salty, slightly fishy | 50.8 |
| 6.2 | $N_2$ purge | Sour dairy, very slight green | Sour dairy, salty, musty (i.e., not fishy) | 50.3 |

Example 7

Preparing Omega-3 Microcapsules Using 275 Bloom Gelatin with Incorporated 200 mg/L $Na_2$EDTA in the Slurry Sodium ethylenediaminetetraacetate ($Na_2$EDTA) (0.2919 g) was dissolved in water (464 g); the pH of the solution was 4.63. Great Lakes pork gelatin (42 g) was then added to the solution (pH 4.73). Next, sodium ascorbate (7.0 g) was added and the pH was 5.23.

High DHA fish oil (73.54 g; XODHA from Ocean Nutrition Canada Ltd.) was added to the gelatin solution and emulsified using a POLYTRON™ homogenizer at 7,500 rpm for 4 minutes. The emulsion was examined under a microscope after emulsification to verify that the oil droplets were small and uniform (about 1-5 μM in diameter).

To a 2 L reactor, of distilled water (855 g) was added and the temperature was maintained at 53° C. The emulsion was added to distilled water in the reactor and the pH was 5.25. Sodium polyphosphate (4.25 g) dissolved in distilled water (80 g) was then added to the diluted emulsion in the reactor. The mixture in the reactor then had a pH of 5.92. Oil droplets were 1-5 μm in diameter and appeared similar to a regular fish-oil-in-gelatin emulsion.

pH was then lowered with 10% phosphoric acid in order to form agglomerations of the primary microcapsules. A normal pork oil microencapsulation process would typically need to be done around pH 4.5-5. In this case, after pH was lowered to 4.67, the oil droplets became 20-40 μm in diameter.

The slurry was then cooled to 5° C. at an average rate of 1° C./5 minutes. When the temperature reached 4° C., a 1% w/w transglutaminase preparation (Ajinomoto USA Inc., Fort Lee, N.J.) was added to the slurry. pH was then adjusted to 6.0 with 10% NaOH. The microcapsules in the slurry were then allowed to be crosslinked and hardened at room temperature (~25° C.) for 16 hours.

The slurry was spray dried and was tested for various quality and stability parameters. The powder was free flowing and had an induction period of 56.4 hours. Although the induction period was similar to a control sample without $Na_2EDTA$, the level of lipid oxidation product measured by peroxide value (PV) was different. The microcapsule powders with and without addition of $Na_2EDTA$ had PV at 1.18 and 2.35 meq/kg, respectively.

Example 8

Preparing Omega-3 Microcapsule with Incorporated Anticaking Agents for Improved Free-Flowing Properties Fish oil microcapsule slurries were prepared following as in Control Example A and tested for final product flowability. Tested drying aids include Hubersorb 600 (J.M. Huber Corp., Harve de Grace, Md.), Zeothix 265 (J.M. Huber Corp.), Capsul modified starch (National Starch & Chemical Co.), and Vitacel cellulose (J. Rettenmaier USA LP, Schoolcraft, Mich.). Examples and resulting powder product flowability are shown in Table 4. It was found that all drying agents improved the free-flowing property of the microcapsules.

TABLE 7

Comparison of powder free-flowing properties

| Example # | Treatment | Appearance of powder |
|---|---|---|
| 8.1 | Control (no anticaking agent) | Fluffy, clumpy powder with some very large clumps |
| 8.2 | Hubersorb 600 (1 g/L) | Fine, free flowing with small clumps |
| 8.3 | Zeothix 265 (1 g/L) | Fine free flowing |
| 8.4 | Capsul (1 g/L) | Fine free flowing |
| 8.5 | Vitacel (1 g/L) | Mostly fine free flowing |

Example 9

Preparing Omega-3 Microcapsule Crosslinked with Glutaraldehyde and with Added Amino Acids A slurry of microcapsules can be prepared as disclosed herein. The slurry can be treated with about 2.5% glutaraldehyde based on gelatin weight to crosslink the microcapsules. Since the MW of glutaraldehyde and lysine are 100 g/mol and 146.2 g/mol, respectively, three times the amount of lysine is needed to neutralize the aldehyde residue. A minimum of 480 mg lysine/kg slurry is then needed (about 0.05% by weight in slurry). Adding 0.25% lysine (or leucine, isoleucine, and other amino acids) has proved to increase induction period from preliminary tests. The hydrophobic amino acids also improved the caking of powder during 30° C./75% RH open dish test. This is then five times reactive amino group in excess. As high as 0.5% amino acids like lysine can be used. The amino acids or proteins can be added just 1-2 hours before the end of crosslinking process.

Example 10

Encapsulation of CoQ10 and Co-Delivered with Omega-3s without Blending with Oil To demonstrate that $CoQ_{10}$ can be delivered in a microcapsule, without blending it with fish oil before microencapsulation, the following examples were performed.

As described herein, fish oil was emulsified into a gelatin solution and the resulting oil droplets agglomerated by complex coacervation with polyphosphate. After agglomeration, an emulsion of $CoQ_{10}$ in gelatin solution was then added at levels of 30-200 mg $CoQ_{10}$ in every 500 mg EPA+DHA delivered. During cooling, the $CoQ_{10}$ droplets became part of the shell and deposited on the surface of the agglomerates. Crosslinking then followed the cooling process to harden the gelatin-based shell.

Below are three examples of loading levels of 30, 100, and 200 mg $CoQ_{10}$ per serving. The powder samples from these experiments had free oil contents below 0.1% and induction period 13.5-14.5 hours tested at 80° C.

Example 10.1

Figure 6:
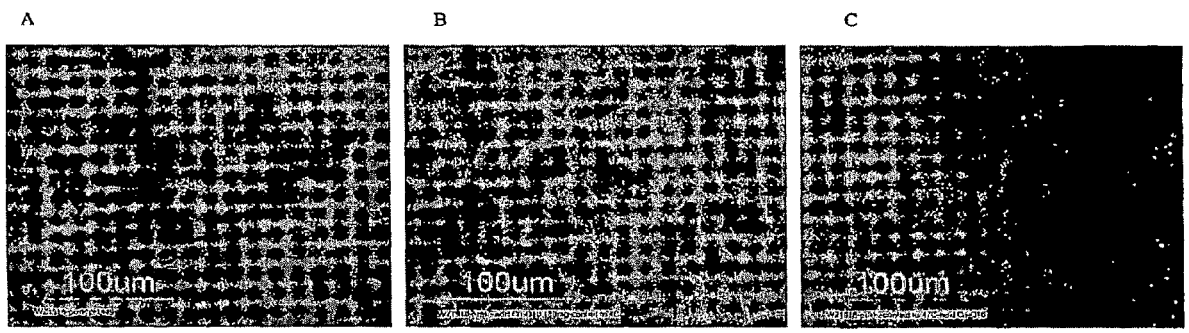
FIG. 6 is a group of micrographs from Example 10.1.

Microencapsulation of DHA Oil with 100 mg $CoQ_{10}$/500 mg EPA/DHA Loading Ratio in Pork Gelatin Shell An amount of 39.1 g of pork gelatin was dissolved in 464.0 g of distilled water at 50° C. A reactor was connected to a circulator and the temperature was set at 50° C. Then, 690.0 g of distilled water were added to the reactor and the temperature was maintained at 50° C. To the gelatin solution, an amount of 72.0 g fish oil was mixed and emulsified at 7500 rpm for 4 minutes. An emulsion formed and contained oil droplets about 1-5 μm in diameter. The emulsion was added to the reactor that contained water at 50° C. The mixture had a pH value of 5.045. Next, 6.4 g of sodium ascorbate were added to the mixture. An aliquot of 85.2 g of 5% w/w sodium polyphosphate solution at room temperature was further added to the reactor. The pH value was adjusted to 4.488 and the agglomeration was allowed to grow up to about 40 μm, as examined by an optical microscope. The multicore, fish-oil particles formed at this stage are shown in FIG. 6A.

16.0 g of pork gelatin were mixed with 184.0 g of distilled water. The gelatin dissolved after it was dispersed in water and heated to and kept at 57° C. Next, 24.0 g of $CoQ_{10}$ powder were added to the gelatin solution and emulsified at 6000 rpm for 2 minutes and 7500 rpm for 1 minute. The $CoQ_{10}$ emulsion formed and contained droplets about 1-5 μm in diameter. Then, 41.0 g of the $CoQ_{10}$ emulsion was mixed into the agglomerated slurry in the reactor at 50° C. The coating of the CoQ$_{10}$ droplets around the multicore fish oil particles was visible as shown in FIG. 6B.

The above suspension containing microcapsule agglomerations was then cooled to 4° C. within 2.5 hours. An enzyme preparation of transglutaminase was added at 0.2% w/w and the temperature was adjusted to 20° C. for enzymatic hardening for at least 12 hours. The finished suspension of microcapsules, as shown in FIG. 6C, was spray dried. The powder of the microcapsules was free flowing and the surface free oil was below 0.1% w/w.

Example 10.2

Figure 7:
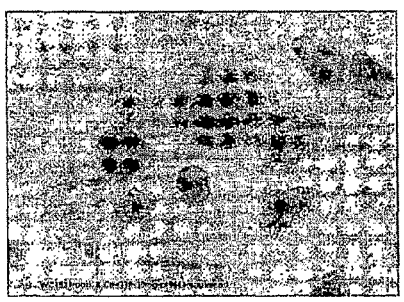
FIG. 7 is a group of micrographs from Example 10.2.
Figure 7:
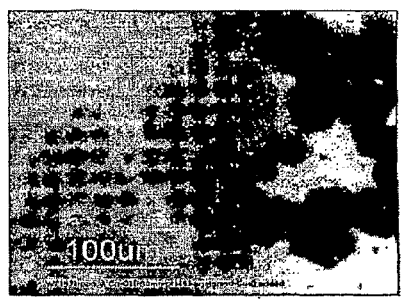

Microencapsulation of DHA Oil with 30 mg Co-Q10/500 mg EPA/DHA Loading Ratio in Pork Gelatin Shell An amount of 41.1 g of pork gelatin was dissolved in 464.0 g of distilled water at 50° C. A reactor was connected to a circulator and the temperature was set at 50° C. 717.0 g of distilled water were added to the reactor and temperature was maintained at 50° C. To this freshly prepared gelatin solution, an amount of 72.0 g fish oil was mixed and emulsified at 7500 rpm for 4 minutes. An emulsion formed and contained oil droplets about 1-5 μm in diameter. The emulsion was added to the reactor that contained water at 50° C. The mixture had a pH value of 5.045. Then, 6.4 g of sodium ascorbate were added to the mixture. An aliquot of 85.2 g of 5% w/w sodium polyphosphate solution at room temperature was further added to the reactor. The pH value was adjusted to 4.488 and the agglomeration was allowed to grow up to about 40 μm, as examined by an optical microscope. The multicore, fish-oil particles formed at this stage is shown in FIG. 7A.

16.0 g of pork gelatin were mixed with 184.0 g of distilled water. The gelatin dissolved after it was dispersed in the distilled water and heated to and kept at 57° C. 24.0 g of CoQ$_{10}$ powder were added to the gelatin solution and emulsified at 6000 rpm for 2 minutes and 7500 rpm for 1 minute. The CoQ$_{10}$ emulsion formed and contained droplets about 1-5 μm in diameter. Then, 12.2 g of the CoQ$_{10}$ emulsion were mixed into the agglomerated slurry in the reactor at 48.3° C. The CoQ$_{10}$-coated microcapsules are shown in FIG. 7B.

The above suspension containing microcapsule agglomerations was then cooled to 4° C. within 2.5 hours. An enzyme preparation of transglutaminase was added at 0.2% w/w and the temperature was adjusted to 20° C. for enzymatic hardening for at least 12 hours. The finished suspension of microcapsules was spray dried. The powder of the microcapsules was free flowing and the surface free oil was below 0.1% w/w.

Example 10.3

Microencapsulation of DHA Oil Using Pork Gelatin with 200 mg Co-Q10/500 mg EPA/DHA Loading Ratio 36.1 g of pork gelatin were mixed with 396.7 g of distilled water. The gelatin dissolved after it was dispersed in the water and heated to and kept at 50° C. A reactor was connected to a circulator and the temperature was set at 50° C. 728.0 g of distilled water were added to the reactor and the temperature was maintained at 50° C. To this freshly prepared gelatin solution, an amount of 72.0 g fish oil was added and emulsified at 7500 rpm for 4 minutes. An emulsion formed and contained oil droplets about 1-5 μm in diameter. The emulsion was added to the reactor that contained water at 50° C.

The mixture had a pH of 5.045. Next, 6.4 g of sodium ascorbate were added to the mixture. An aliquot of 85.2 g of 5% w/w sodium polyphosphate solution at room temperature was further added to the reactor. The pH value was adjusted to 4.488, which allowed the agglomeration to grow up to about 40 μm, as examined by an optical microscope.

Figure 8:
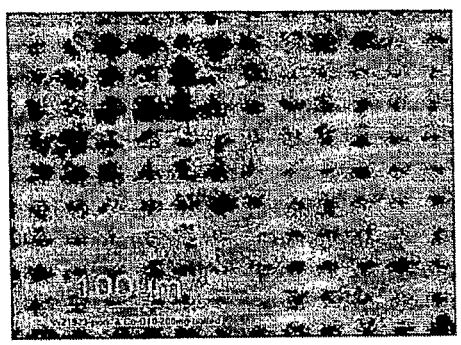
FIG. 8 is a micrograph of the finished $CoQ_{10}$-coated microcapsules (with a loading of 200 mg $CoQ_{10}$/500 mg EPA/DHA) from Example 10.3.

16.0 g of pork gelatin were mixed with 184.0 g of distilled water. The gelatin dissolved after it was dispersed in water and heated to and kept at 57° C. Next, 24.0 g of CoQ$_{10}$ powder was added to the gelatin solution and emulsified at 6000 rpm for 2 minutes and 7500 rpm for 1 minute. The CoQ$_{10}$ emulsion formed and contained droplets of about 1-5 μm in diameter. Next, 82.0 g of the CoQ$_{10}$ emulsion were mixed into the agglomerated slurry in the reactor at 48.3° C. The above suspension containing microcapsule agglomerations was then cooled to 4° C. within 2.5 hours. An enzyme preparation of transglutaminase was added at 0.2% w/w and the temperature was adjusted to 20° C. for enzymatic hardening for at least 12 hours. The finished suspension of microcapsules, as shown in FIG. 8, was spray dried. The powder of the microcapsules was free flowing and the surface free oil was below 0.1% w/w.

Example 11

Co-Delivery of Zinc and Fish Oil in Microcapsule Powder

The omega-3 microcapsule powder used had an average 180.5 mg/g powder of DHA+EPA and 210.9 mg/g powder of total omega-3s. In order to deliver zinc at 2, 5, 10, 50, and 100 mg per 500 mg EPA+DHA of powder, ZnCl$_2$ was added to the finished slurry before spray drying. The formulations used are described in (Table 8).

TABLE 8

Designed microcapsules with various levels of zinc

| mg Zn/500 mg (DHA + EPA) | mg Zn/g powder | mg ZnCl$_2$/ g powder | Formulated ZnCl$_2$ mg/g powder | ZnCl$_2$ in 100 g slurry |
| --- | --- | --- | --- | --- |
| 2 | 0.72 | 1.50 | 1.91 | 0.017 |
| 5 | 1.81 | 3.76 | 4.77 | 0.042 |
| 10 | 3.61 | 7.52 | 9.53 | 0.085 |
| 50 | 18.05 | 37.62 | 47.67 | 0.424 |
| 100 | 36.10 | 75.24 | 95.33 | 0.848 |

Slurry total solid content (%): 8.90

Example 11.1

Preparing Base Slurry of Fish Oil Microcapsule Using 240 Bloom Fish Gelatin

An omega-3 fish oil microcapsule was prepared by dissolving 44 g of 240 Bloom fish gelatin in 320 g of water. This solution was then heated to 40° C. An amount of 7.3 g sodium ascorbate was added to the gelatin solution. Solution pH increased from 5.385 to 5.650. Then, 72.0 g of a high DHA fish oil (OXDHA, Ocean Nutrition Canada Ltd., Dartmouth, NS) were added to the gelatin solution and was then emulsified at 7500 rpm for 4 minutes with a high speed Polytron homogenizer. The emulsion was examined under a microscope after emulsification and verified that the oil droplets were small and uniform (about 1-5 μm in diameter). 1051 g of distilled water were added to a 2 L reactor and temperature was maintained at 40° C. The emulsion was added to the distilled water in the reactor and pH of the mixture was found to be 5.662 at 39.6° C. Next, 4.4 g of sodium polyphosphate were dissolved in 84 g of distilled water and added to the diluted emulsion in the reactor. The mixture in the reactor had a pH value of 6.401 pH was then lowered with 10% phosphoric acid in order to form agglomeration of the primary microcapsules. After pH was lowered to 4.459, the secondary microcapsule agglomeration had a size of 30-70 µm in diameter. The slurry was then cooled from 40° C. to 5° C. at an average rate of 1° C./5 min. After pH was adjusted to 6.0, 1% transglutaminase was added to the slurry for crosslinking and hardening the shell at 5° C. for 1 hour, 15° C. for 8 hours, and 20° C. for 9 hours.

The preceding steps were carried out for four identical slurry samples. The slurries were blended after crosslinking. One liter of the blended slurry was then spray dried to produce a free flowing powder. This sample had omega-3 oil only and no zinc for delivery. Lipid analysis showed that the powder had 129 mg DHA/g, 31 mg EPA/g, and a total omega-3 at 176 mg/g powder.

Example 11.2

Preparing Omega-3 Microcapsules Using 240 Bloom Gelatin with Incorporated Zinc into the Slurry The zinc-omega-3 microcapsules were prepared using 240 Bloom gelatin as described above for Example 11.1. One liter of the blended slurry was sampled and stirred on a magnetic stirrer. An amount of 0.15 g $ZnCl_2$ was dissolved in the slurry. After mixing for 30 minutes, the slurry was then spray dried to produce a free flowing powder containing omega-3 oil as well as zinc for delivery. Various amounts of $ZnCl_2$ (0.38, 0.76, 3.81 and 7.63 g, respectively) were incorporated into 1 L of the blended slurry resulting in different levels of zinc for delivery. These are listed as Examples 11.2.1 to 11.2.5. The results of zinc and analysis are shown in Table 9.

TABLE 9

Comparison of zinc levels of the powder samples

| Example # | Zinc (mg/g) | Zinc (mg/500 mg EPA + DHA) |
| --- | --- | --- |
| 11.1 | 0.006 | 0.02 |
| 11.2.1 | 1.1 | 3.4 |
| 11.2.2 | 2.3 | 7.3 |
| 11.2.3 | 3.7 | 11.6 |
| 11.2.4 | 18.5 | 57.8 |
| 11.2.5 | 32.7 | 102.2 |

Figure 9:
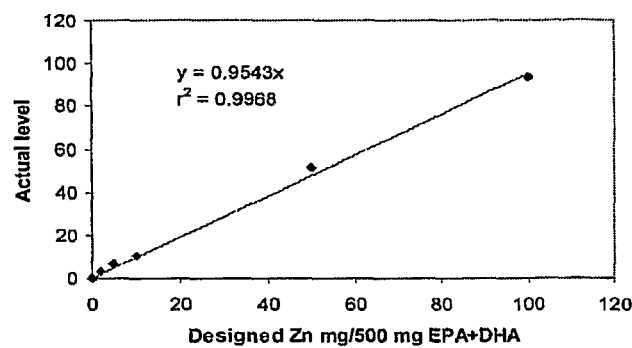
FIG. 9 is a graph showing the prediction of zinc level in fish oil powder by co-spray drying $ZnCl_2$ with the microcapsule slurry.

The amount of zinc in the microcapsule powder was well predicted by the amount added to the slurry before spray drying (FIG. 9).

Specific Embodiments

Disclosed herein is a microcapsule comprising an agglomeration of primary microcapsules and a loading substance, each individual primary microcapsule having a primary shell, wherein the loading substance is encapsulated by the primary shell, wherein the agglomeration is encapsulated by an outer shell, and wherein the primary shell, the outer shell, or both comprise a residue of one or more compositions comprising an amino acid, protein, saccharide, wax, or combination thereof. Also disclosed is a single-core microcapsule, comprising a core, wherein the core comprises a loading substance, a primary shell surrounding the core, and an outer shell surrounding the primary shell, wherein the primary shell, the outer shell, or both comprise a residue of one or more compositions comprising an amino acid, protein, saccharide, wax, or combination thereof.

Also disclosed is a process for preparing a microcapsule comprising providing an emulsion comprising a first polymer component, a loading substance, a second polymer component, and a composition comprising one or more of an amino acid, a protein, a saccharide, a wax, or combination thereof; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; and further cooling the aqueous mixture to form an outer shell around the agglomeration, wherein the primary shell material, the outer shell, or both comprises the saccharide, the wax, or combination thereof.

Still further, disclosed is a process for preparing a microcapsule comprising providing a slurry of one or more microcapsules, wherein the microcapsule comprises a shell material and a loading substance; adding a composition comprising one or more of an amino acid, protein, saccharide, wax, an antioxidant, or zinc or combinations thereof to the slurry; and then drying the slurry.

Further, disclosed herein is a process for preparing a microcapsule comprising providing an emulsion comprising a first polymer component, a loading substance, and a second polymer component; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; adding an composition comprising one or more of an amino acid, a protein, a saccharide, or a wax to the aqueous mixture; and further cooling the aqueous mixture to form an outer shell around the agglomeration, wherein the primary shell material, the outer shell, or both comprises the saccharide.

Also, disclosed is a process for preparing a microcapsule comprising providing an emulsion comprising a first polymer component, a loading substance, a second polymer component, and a chelator to the emulsion; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; and further cooling the aqueous mixture to form an outer shell around the agglomeration.

Also disclosed is a composition comprising a spray dried emulsion comprising a first polymer component and a loading substance, and a residue of one or more compositions comprising an amino acid, protein, saccharide, wax, or combination thereof.

Further, disclosed is a formulation vehicle comprising any of the microcapsules disclosed herein. The formulation vehicle can be a foodstuff, a beverage, a nutraceutical formulation, or a pharmaceutical formulation. Also disclosed is a sachet comprising any of the microcapsules disclosed herein.

Still further, disclosed is a method of delivering a loading substance to a subject, comprising administering to the subject any of the microcapsules disclosed herein, or any of the formulation vehicles disclosed herein. The subject can be a mammal. The subject can be a human. The loading substance can comprise an omega-3 fatty acid, an alkyl ester of an omega-3 fatty acid, a triglyceride ester of an omega-3 fatty acid, a phytosterol ester of an omega-3 fatty acid, and/or a mixture thereof. Also disclosed is a use of any of the microcapsules disclosed herein to prepare a medicament for delivering a loading substance to a subject.

The microcapsule can be prepared by the method comprising providing an emulsion comprising a first polymer component, a loading substance, and a second polymer component; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; and further cooling the aqueous mixture to form an outer shell around the agglomeration.

The disclosed microcapsules can have an induction period of greater than about 40 hours, greater than about 50 hours, greater than about 75 hours, or greater than about 100 hours.

The composition can comprise the amino acid and the ratio of the amino acid to the second polymer component can be about 1:5 to about 5:1. The one or more compositions can comprise the amino acid leucine, isoleucine, methionine, cysteine, tyrosine, tryptophan, phenylalanine, or a mixture thereof. The one or more compositions can comprise the amino acid lysine. The one or more compositions can comprise the amino acid glutamine. The one or more compositions can comprise the amino acids leucine, isoleucine, methionine, cysteine, tyrosine, tryptophan, phenylalanine, or a mixture thereof and glutamine. The one or more compositions can comprise milk protein. The one or more compositions can comprise whey protein, whey protein isolate, or whey protein concentrate; the whey protein can be combined with glycerin.

The composition can comprise the protein and the ratio of the protein to the second polymer component can be about 1:1 to about 40:1. The protein can be milk protein, gelatin, whey protein isolate, whey protein concentrate, caseinate, soy protein, BSA, or a mixture thereof. The composition can comprise whey protein, whey protein isolate, or whey protein concentrate. The whey protein can be combined with glycerin.

The composition can comprise the saccharide and the ratio of the saccharide to the second polymer component can be from about 1:0.02 to about 1:0.5. The composition can comprise the saccharide and the ratio of saccharide to the total shell material can be from about 1:0.2 to about 1:5.

The one or more compositions can comprise a saccharide having a molecular weight of greater than about 100,000 Daltons or less than about 100,000 Daltons. The one or more compositions can comprise the saccharide chitosan. The one or more compositions can comprise chitosan and glutamine, chitosan, lysine, and glutamine, chitosan, glutamine and one or more of leucine, isoleucine, methionine, cysteine, tyrosine, tryptophan, or phenylalanine, or chitosan and one or more of leucine, isoleucine, methionine, cysteine, tyrosine, tryptophan, or phenylalanine. The one or more compositions can comprise the saccharide starch; the starch can be a modified starch. The one or more compositions can comprise the saccharide lactose. The one or more compositions can comprise the saccharides starch and lactose. The one or more compositions can comprise the saccharide in the form of maple syrup, honey, corn syrup, or mixtures thereof. The one or more compositions can comprise the saccharide sucrose. The one or more compositions can comprise the saccharide hydroxypropylmethylcellulose. The one or more compositions can comprise the saccharide maltodextrin, oligofructans, cyclodextrins, carboxymethylcellulose, ethylcellulose, hydroxypropylcellulose, cellulose ether, agar, alginate, pectin, low-methoxyl-pectin, gum arabic, carrageenan, cellulose gum, dilutan gum, gellan gum, locus bean gum, welan gum, xanthan gum, or a mixture thereof. The one or more compositions can comprise the saccharide glucose, fructose, galactose, arabinose, ribose, ribulose, xylose, xylulose, cellobiose, mannose, xylose, ribose, sorbose, cellotriose, trehalose, maltose, raffinose, xylitol, sorbitol, isomalt, glucosamine, or mixtures thereof. The saccharide can be added after cooling but before further cooling the aqueous mixture to form an outer shell around the agglomeration.

The one or more compositions can comprise the wax carnauba wax. The composition can comprise the wax carnauba wax in a microemulsion form. The one or more compositions can comprise the wax candelilla, cersines, Japan wax, orange peel wax, rice bran wax, shellac, paraffin, montan, microcrystalline wax, polyethylene, beeswax, or a mixture thereof. The one or more compositions can further comprise a surfactant. The composition can comprise the wax and the ratio of the wax to the second polymer component is about 1:1 to about 1:10.

The one or more compositions can comprise an antioxidant. The antioxidant can comprise coenzyme Q10, lutein, zeaxanthan, carotene (e.g., beta-carotene), or mixtures thereof.

The disclosed microcapsules can further comprising a chelator. The chelator can be disodium ethylenediamine tetraacetic acid. The chelator can comprise one or more of citric acid, phytic acid, malic acid, tartaric acid, oxalic acid, succinic acid, polyphosphoric acids, or mixtures thereof. The chelator can be added to the emulsion and/or the aqueous mixture.

The disclosed microcapsules can further comprise an anticaking compound. The anticaking compound can be added to the microcapsule before, during, or after drying.

An antioxidant can be added to the emulsion and/or the aqueous mixture. The antioxidant can comprise a phenolic compound, a plant extract, or a sulphur-containing compound. The antioxidant can comprise ascorbic acid or a salt thereof.

The composition can further comprise a surfactant.

The primary shell or the outer shell, or both primary and outer shells can comprise a surfactant, gelatin, polyphosphate, saccharide, or a mixture thereof. The primary shell or the outer shell, or both primary and outer shells can comprise gelatin type B, polyphosphate, gum arabic, alginate, chitosan, carrageenan, pectin, low-methoxyl-pectin, starch, modified starch, alpha-lactalbumin, beta-lactoglobulin, ovalbumin, polysorbiton, maltodextrin, cyclodextrin, cellulose, methyl cellulose, ethyl cellulose, hydropropylmethylcellulose, carboxymethylcellulose, milk protein, whey protein, soy protein, canola protein, albumin, kosher gelatin, non-kosher gelatin, Halal gelatin, non-Halal gelatin, or a mixture thereof. The primary shell or the outer shell or both primary and outer shells can comprise an antioxidant. The primary or the outer shell or both primary and outer shells can comprise zinc.

The primary shell or the outer shell, or both primary and outer shells can comprise gelatin type A. The primary shell or the outer shell, or both primary and outer shells can comprise fish gelatin. The primary shell or the outer shell, or both primary and outer shells can comprise pork gelatin. The primary shell or the outer shell, or both primary and outer shells can comprise a gelatin with a Bloom number of from about 0 to about 300. The primary shell or the outer shell, or both primary and outer shells can comprise a gelatin with a Bloom number of from about 0 to about 50. The primary shell or the outer shell, or both primary and outer shells can comprise a gelatin with a Bloom number of from about 51 to about 300. The primary shell or the outer shell, or both primary and outer shells can comprise a gelatin with a Bloom number of about 0, about 210, about 220, or about 240. The primary shell or the outer shell, or both primary and outer shells can comprise a complex coacervate. The primary shell or the outer shell, or both primary and outer shells can comprise a complex coacervate of gelatin and polyphosphate. The primary shell material and the outer shell can comprise a complex coacervate between gelatin and polyphosphate. The primary shell material and the outer shell can comprise a complex coacervate between gelatin and alginate, gelatin and pectin, gelatin and gum arabic, gelatin and xanthan, gelatin and low methoxyl pectin, or gelatin and whey protein.

The first polymer component can comprise a surfactant, gelatin, polyphosphate, saccharide, or a mixture thereof. The first polymer component can comprise gelatin type B, polyphosphate, gum arabic, alginate, chitosan, carrageenan, pectin, low-methoxyl-pectin, starch, modified starch, alpha-lactalbumin, beta-lactoglobumin, ovalbumin, polysorbiton, maltodextrin, cyclodextrin, cellulose, methyl cellulose, ethyl cellulose, hydropropylmethylcellulose, carboxymethylcellulose, milk protein, whey protein, soy protein, canola protein, albumin, kosher gelatin, non-kosher gelatin, Halal gelatin, non-Halal gelatin, or a mixture thereof. The first polymer component can comprise gelatin type A. The first polymer component can comprise fish gelatin. The first polymer component can comprise pork gelatin. The first polymer component can have a Bloom number of from about 0 to about 300. The first polymer component can have a Bloom number of from about 0 to about 50. The first polymer component can have a Bloom number of from about 51 to about 300. The first polymer component can have a Bloom number of about 0, about 210, about 220, or about 240.

The second polymer component can comprise a surfactant, gelatin, polyphosphate, saccharide, or a mixture thereof. The second polymer component can comprise gelatin type A, gelatin type B, polyphosphate, gum arabic, alginate, chitosan, carrageenan, pectin, low-methoxyl-pectin, starch, modified starch, alpha-lactalbumin, beta-lactoglobumin, ovalbumin, polysorbiton, maltodextrin, cyclodextrin, cellulose, methyl cellulose, ethyl cellulose, hydropropylmethylcellulose, carboxymethylcellulose, milk protein, whey protein, soy protein, canola protein, albumin, kosher gelatin, non-kosher gelatin, Halal gelatin, non-Halal gelatin, or a mixture thereof. The second polymer component can comprise polyphosphate.

The loading substance can comprise a biologically active substance, a nutritional supplement, a microbial oil, marine oil, algal oil, oil from a dinoflagellate, oil from *Crypthecodinium cohnii*, fungal oil, oil from *Thraustochytrium, Schizochytrium*, or a mixture thereof, or plant oil.

The loading substance can comprise fish oil, such as an Atlantic fish oil, Pacific fish oil, Mediterranean fish oil, light pressed fish oil, alkaline treated fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonid oil, or shark oil. The loading substance can comprise a non-alkaline treated fish oil. The loading substance can comprise arachidonic acid. The loading substance can comprise an omega-3 fatty acid, an alkyl ester of an omega-3 fatty acid, a triglyceride ester of an omega-3 fatty acid, a phytosterol ester of an omega-3 fatty acid, and/or a mixture thereof. The loading substance can comprise docosahexaenoic acid and/or eicosapentaenoic acid, a $C_1$-$C_6$ alkyl ester thereof, a triglyceride ester thereof, a phytosterol ester thereof, and/or a mixture thereof.

In the disclosed microcapsules, the outer shell can have an average diameter of from about 1 μm to about 2,000 μm, from about 20 μm to about 1,000 μm, or from about 30 μm to about 80 μm. The primary can have an average diameter of from about 40 nm to about 10 μm or from about 0.1 μm to about 5 μm. The loading substance can be from about 20% to about 90% or from about 50% to about 70% by weight of the microcapsule.

In the disclosed methods any or all of steps can be preformed under a nitrogen atmosphere.

The disclosed methods can further comprise adding a transglutaminase. The disclosed methods can further comprise adding glutaraldehyde.

The disclosed methods can further comprise drying the microcapsules. The microcapsules can be spray dried. The microcapsules can be spray dried in the presence a carbohydrate.

In the disclosed methods, the emulsion can be prepared by emulsifying at from about 1,000 to about 15,000 rpm. The emulsion can further comprise a composition comprising a saccharide, a wax, or combination thereof.

In the disclosed methods, cooling can be at a rate of about 1° C. per about 1 to about 100 minutes or a rate of about 1° C./5 minute. The mixture can be cooled until it reaches a temperature of from about 5° C. to about 10° C. or about 5° C.

A microcapsule prepared according to the disclosed methods is also disclosed herein.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A microcapsule, comprising an agglomeration of primary microcapsules and a loading substance, each individual primary microcapsule having a primary shell, wherein the loading substance is encapsulated by the primary shell, wherein the agglomeration is encapsulated by an outer shell, wherein the primary and outer shell is a complex coacervate of gelatin and polyphosphate and wherein the primary shell, the outer shell, or both comprise an additional composition that is not part of the complex coacervate, said additional composition being selected from the group consisting of glucose, fructose, galactose, arabinose, ribose, ribulose, xylose, mannose, xylulose, sucrose, lactose, cellobiose, sorbose, trehalose, maltose, xylitol, sorbitol, isomalt, and glucosamine.

2. The microcapsule of claim 1, further comprising a chelator, wherein the chelator comprises one or more of citric acid, phytic acid, malic acid, tartaric acid, oxalic acid, succinic acid, polyphosphoric acids, disodium ethylenediamine tetraacetic acid, or a mixture thereof.

3. The microcapsule of claim 1, wherein the loading substance comprises a biologically active substance.

4. The microcapsule of claim 1, wherein the loading substance comprises microbial oil, marine oil, algal oil, oil from a dinoflagellate, fungal oil, plant oil, oil from *Crypthecodinium cohnii*, oil from *Thraustochytrium, Schizochytrium*, or a mixture thereof.

5. The microcapsule of claim 1, wherein the loading substance comprises fish oil.

6. The microcapsule of claim 1, wherein the loading substance comprises an omega-3 fatty acid, an alkyl ester of an omega-3 fatty acid, a triglyceride ester of an omega-3 fatty acid, a phytosterol ester of an omega-3 fatty acid, and/or a mixture thereof.

7. The microcapsule of claim 1, wherein the loading substance comprises docosahexaenoic acid and/or eicosapentaenoic acid, a $C_1$-$C_6$ alkyl ester thereof, a triglyceride ester thereof, a phytosterol ester thereof, and/or a mixture thereof.

8. The microcapsule of claim 1, wherein the loading substance is from 20% to 90% by weight of the microcapsule.

9. The microcapsule of claim 1, wherein the loading substance is from 50% to 70% by weight of the microcapsule.

10. The microcapsule of claim 1, wherein the primary shell has an average diameter of from 40 nm to 10 μm.

11. The microcapsule of claim 1, wherein the primary shell has an average diameter of from 0.1 μm to 5 μm.

12. The microcapsule of claim 1, wherein the outer shell has an average diameter of from 20 μm to 1,000 μm.

13. The microcapsule of claim 1, wherein the outer shell has an average diameter of from 30 μm to 80 μm.

14. The microcapsule of claim 1, wherein the composition further comprises an antioxidant and the antioxidant comprises coenzyme $Q_{10}$, lutein, zeaxanthan, carotene, or a mixture thereof.

15. The microcapsule of claim 1, wherein the gelatin comprises gelatin type A.

16. The microcapsule of claim 1, wherein the gelatin comprises fish gelatin.

17. The microcapsule of claim 1, wherein the gelatin comprises pork gelatin.

* * * * *